(12) United States Patent
Thompson

(10) Patent No.: US 6,448,009 B1
(45) Date of Patent: *Sep. 10, 2002

(54) METHOD FOR TARGET SITE SELECTION AND DISCOVERY

(75) Inventor: James D. Thompson, Boulder, CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/676,807

(22) Filed: Sep. 29, 2000

Related U.S. Application Data

(63) Continuation of application No. 09/112,086, filed on Jul. 8, 1998, now Pat. No. 6,183,959, which is a continuation-in-part of application No. 09/108,087, filed on Jun. 30, 1998, now abandoned.
(60) Provisional application No. 60/051,718, filed on Jul. 3, 1997.

(51) Int. Cl.$^7$ ............... C12Q 1/68; C12N 15/09
(52) U.S. Cl. ............... 435/6; 435/29; 435/91.31; 536/24.5
(58) Field of Search ............... 435/6, 29, 91.31, 435/252.3, 375, 419, 455, 468, 471, 489; 514/44; 536/24.3, 24.31, 24.32, 24.5

(56) References Cited

U.S. PATENT DOCUMENTS

| | | |
|---|---|---|
| 4,693,976 A | 9/1987 | Schilperoort et al. |
| 4,762,785 A | 8/1988 | Comai |
| 4,940,838 A | 7/1990 | Schilperoort et al. |
| 4,987,071 A | 1/1991 | Cech et al. |
| 5,004,863 A | 4/1991 | Umbeck et al. |
| 5,149,645 A | 9/1992 | Hoekema et al. |
| 5,159,135 A | 10/1992 | Umbeck et al. |
| 5,164,310 A | 11/1992 | Smith et al. |
| 5,177,010 A | 1/1993 | Goldman et al. |
| 5,217,889 A | 6/1993 | Roninson et al. |
| 5,231,019 A | 7/1993 | Paszkowski et al. |
| 5,334,711 A | 8/1994 | Sproat et al. |
| 5,464,763 A | 11/1995 | Schilperoort et al. |
| 5,478,369 A | 12/1995 | Albertsen et al. |
| 5,496,698 A | 3/1996 | Draper et al. |
| 5,525,468 A | 6/1996 | McSwiggen et al. |
| 5,595,873 A | 1/1997 | Joyce |
| 5,616,459 A | 4/1997 | Kramer et al. |
| 5,624,803 A | 4/1997 | Noonberg et al. |
| 5,631,146 A | 5/1997 | Szostak et al. |
| 5,631,359 A | 5/1997 | Chowrira et al. |
| 5,633,133 A | 5/1997 | Long et al. |
| 6,183,959 B1 * | 2/2001 | Thompson ............... 435/6 |

FOREIGN PATENT DOCUMENTS

| | | |
|---|---|---|
| DE | 44 24 762 C1 | 7/1995 |
| EP | 0 120 516 A2 | 10/1984 |
| EP | 0 131 624 B1 | 1/1985 |
| EP | 0 159 418 B1 | 10/1985 |
| EP | 0 176 112 A1 | 4/1986 |
| EP | 0 267 159 A2 | 5/1988 |
| EP | 0 290 799 A2 | 11/1988 |
| EP | 0 292 435 B1 | 11/1988 |
| EP | 0 320 500 A2 | 6/1989 |
| EP | 0 360 257 A2 | 3/1990 |
| EP | 0 604 662 A1 | 7/1993 |
| EP | 0 116 718 B2 | 8/1994 |
| EP | 0 627 752 A1 | 12/1994 |
| WO | 90/08828 | 8/1990 |
| WO | 91/03162 | 3/1991 |
| WO | 92/07065 | 4/1992 |
| WO | 93/15187 | 8/1993 |
| WO | 93/23569 | 11/1993 |
| WO | 94/02595 | 2/1994 |
| WO | 95/23225 | 8/1995 |
| WO | 96/01314 | 1/1996 |
| WO | 96/18736 | 6/1996 |
| WO | 97/30581 | 8/1997 |
| WO | 98/32880 | 7/1998 |

OTHER PUBLICATIONS

Abramovitz et al., "Catalytic Role of 2'-Hydroxyl Groups Within a Group II Intron Active Site," *Science* 271:1410–1413 (1996).

Banerjee and Turner, "The Time Dependence of Chemical Modification Reveals Slow Steps in the Folding of a Group I Ribozyme," *Biochemistry* 34:6504–6512 (1995).

Bartel and Szostak, "Isolation of New Ribozymes From a Large Pool of Random Sequences," *Science* 261:1411–1418 (1993).

Beaudry and Joyce, "Directed Evolution of an RNA Enzyme," *Science* 257:635–641 (1992).

Beigelman et al., "Chemical Modification of Hammerhead Ribozymes," *J. Biol. Chem.* 270:25702–25708 (1995).

Berzal–Herranz et al., "Essential nucleotide sequences and secondary structure elements of the hairpin ribozyme," *EMBO J.* 12:2567–2574 (1993).

Berzal–Herranz et al., "In vitro selection of active hairpin ribozymes by sequential RNA–catalyzed clevage and ligation reactions," *Genes & Development* 6:129–134 (1992).

Bevilacqua et al., "A Mechanistic Framework for the Second Step of Splicing Catalyzed by the Tetrahymena Ribozyme," *Biochemistry* 35:648–658 (1996).

Bourque, "Antisense strategies for genetic manipulations in plants," *Plant Science* 105:125–149 (1995).

Breaker and Joyce, "Inventing and improving ribozyme function: rational design versus iterative selection methods," *TIBTECH* 12:268–275 (1994).

(List continued on next page.)

*Primary Examiner*—Andrew Wang
*Assistant Examiner*—Thomas G. Larson
(74) *Attorney, Agent, or Firm*—McDonnell Boehnen Hulbert & Berghoff

(57) ABSTRACT

Nucleic acid catalysts, method of screening/selection for nucleic acid catalysts, synthesis of ribozyme libraries and discovery of gene sequences involved in a biological process are described.

39 Claims, 20 Drawing Sheets

OTHER PUBLICATIONS

Breaker et al., "DNA Enzymes," *Nature Biotechnology* 15:427–431 (1997).

Breaker, "Are engineered proteins getting competition from RNA?" *Current Opinion in Biotechnology* 7:442–448 (1996).

Burgin et al., "Chemically Modified Hammerhead Ribozymes with Improved Catalytic Rates," *Biochemistry* 35:14090–14097 (1996) (volume no mistakenly listed as 6).

Campbell and Cech, "Identification of ribozymes within a ribozyme library that efficiently cleaves a long substrate RNA," *RNA* 1:598–608 (1995).

Cech, "Ribozymes and Their Medical Implications," *JAMA* 260:3030–3034 (1988).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Chowrira et al., "Novel guanosine requirement for catalysis by the hairpin ribozyme," *Nature* 354:320–322 (1991).

Christoffersen and Marr, "Riobozymes as Human Therapeutic Agents," *J. Med. Chem.* 38:2023–2037 (1995) (also referred to as Christofferson and Marr).

Christoffersen, "Translating genomics information into therapeutics: A Key Role for Oligonucleotides," *Nature Biotechnology* 15:483–484 (1997) (Christofferson).

Cotten, "The in vivo application of ribozymes," *TIBTECH* 8:174–178 (1990).

Couture and Stinchcomb, "Anti–gene therapy: the use of ribozymes to inhibit gene function," *Trends In Genetics* 12:510–515 (1996).

Daniels et al., "Two Competing Pathways for Self–splicing by Group II Introns: A Quantitative Analysis of in Vitro Reaction Rates and Products," *J. Mol. Biol.* 256:31–49 (1996).

Dropulic et al., "Functional Characterization of a U5 Ribozyme: Intracellular Suppression of Human Immunodeficiency Virus Type I Expression," *Journal of Virology* 66:1432–1441 (1992).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Forster and Altman, "External Guide Sequences for an RNA Enzyme," *Science* 249:783–786 (1990).

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Good et al., "Expression of small, therapuetic RNAs in human nuclei," *Gene Therapy* 4:45–54 (1997).

Grasby et al., "Purine Functional Groups in Essential Residues of the Hairpin Ribozyme Required for Catalytic Cleavage of RNA," *Biochemistry* 34:4068–4076 (1995).

Griffin et al., "Group II intron ribozymes that cleave DNA and RNA linkages with similar efficiency, and lack contacts with substrate 2'–hydroxyl groups," *Chemistry & Biology* 2:761–770 (1995).

Guerrier–Takada et al., "The RNA Moiety of Ribonuclease P Is the Catalytic Subunit of the Enzyme," *Cell* 35:849–857 (1983).

Guo and Collins, "Efficent trans–cleavage of a stem–loop RNA substrate by a ribozyme derived from Neurospora VS RNA," *EMBO J.* 14:368–376 (1995).

Hampel and Tritz, "RNA Catalytic Properties of the Minimum (–)sTRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

Harris et al., "Identification of phosphates involved in catalysis by the ribozyme RNase P RNA," *RNA* 1:210–218 (1995).

Haseloff and Gerlach, "Simple RNA Enzymes with New and Highly Specific Endoribonuclease Activities," *Nature* 334:585–591 (1988).

Hegg et al., "Kinetics and Thermodynamics of Intermolecular Catalysis by Hairpin Ribozymes," *Biochemistry* 34:15813–15828 (1995).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

Herschlag and Cech, "Catalysis of RNA Cleavage by the *Tetrahymena thermophila* Ribozyme. 2. Kinetic Description of the Reaction of an RNA Substrate That Forms a Mismatch at the Active Site," *Biochemistry* 29:10172–10180 (1990).

Izant and Weintraub, "Constitutive and Conditional Suppression of Exogenous and Endogeneous Genes by Anti–Sense RNA," *Science* 229:345–352 (1985).

Jarvis et al., "Inhibition of Vascular Smooth Muscle Cell Proliferation by Hamnmerhead Ribozymes Targeting C–Myb" *Journal of Cellular Biochemistry* 19A:221 (1995) (Abstract Only XP 002024063).

Jeffries and Symons, "A Catalytic 13–mer Ribozyme," *Nucleic Acids Research* 17:1371–1377 (1989).

Jorgensen, "Cosuppression, Flower Color Patterns, and Metastable Gene Expression States," *Science* 268:686–691 (1995).

Joseph et al., "Substrate selection rules for the hairpin ribozyme determined by in vitro selection, mutation, and analysis of mismatched substrates," *Genes & Development* 7:130–138 (1993).

Joyce et al., "Amplification, mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–ras Ribozyme," *Antisense Research & Development* 2:3–15 (1992).

Knitt et al., "ph Dependencies of the Tetrahymena Ribozyme Reveal an Unconvential Origin of an Apparent $pK_a$," *Biochemistry* 35:1560–1570 (1996).

Kumar and Ellington, "Artificial evolution and natural ribozymes," *FASEB J.* 9:1183–1195 (1995).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Li et al., "Thermodynamic and Activation Parameters for Binding of a Pyrene–Labeled Substrate by the Tetrahymena Ribozyme: Docking is Not Diffusion–Controlled and is Driven by a Favorable Entropy Change," *Biochemistry* 34:14394–14399 (1995).

Lieber and Strauss, Selection of Efficient Cleavage Sites in Target RNAs by Using a Ribozyme Expression Library, *Mol. Cellular Biol.* 15:540–551 (1995).

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA," *Nucleic Acids Research* 22(12):2183–2196 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

McGarry and Lindquist, "Inhibition of heat shock protein synthesis by heat–inducible antisense RNA," *Proc. Natl. Acad. Sci. USA* 83:399–403 (1986).

Michel et al., "Structure and Activities of Group II Introns," *Annu. Rev. Biochem.* 64:435–461 (1995).

Michel and Westhof, "Slippery substratrates," *Nat. Struct. Biol.* 1:5–7 (1994).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan and Uhlenbeck, "Synthesis of Small RNAs Using T7 RNA Polymerase," *Methods Enzymol.* 180:51–62 (1989).

Nathans and Smith, "Restriction Endonucleases in the Analysis and Restructuring of DNA Molecules," *Ann. Rev. Biochem.* 44:273–293 (1975).

Noonberg et al., In vivo generation of highly abundant sequence–specific oligonucleotides for antisense and triplex gene regulation, *Nucleic Acids Research* 22(14):2830–2836 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Orgel, "Selection in vitro," *Proc. R. Soc. London B.* 205:435–442 (1979).

Pan et al., "Probing of tertiary interactions in RNA: 2'–Hydroxyl–base contacts between the Rnase P and pre–tRNA," *Proc. Natl. Acad. Sci. USA* 92:12510–12514 (1995).

Perreault et al., "Mixed Deoxyribo– and Ribo–Oligonucleotides with Catalytic Activity," *Nature* 344:565–567 (1990) (often mistakenly listed as Perrault).

Perrotta and Been, "A pseudoknot–like structure required for efficeint self–cleavage of hepatitis delta virus RNA," *Nature* 350:434–436 (1991).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Puttaraju et al., "A circular trans–acting hepatitis delta virus ribozyme," *Nucleic Acids Research* 21:4253–4258 (1993).

Pyle et al., "Building a Kinetic Framework for Group II Intron Ribozyme Activity: Quantitation of Interdomain Binding and Reaction Rate," *Biochemistry* 33:2716–2725 (1994).

Robertson et al., "Purification and Properties of a Specific *Escherichia coli* Riobnuclease which Cleaves a Tyrosine Transfer Ribonucleic Acid Precursor," *J. Biol. Chem.* 247:5243–5251 (1972).

Rossi et al., "Ribozymes as Anti–HIV–1 Therapeutic Agents: Principles, Applications, and Problems," *Aids Research and Human Retroviruses* 8:183–189 (1992).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Schmidt et al., "Base and sugar requirements for RNA cleavage of essential nucleoside residues in internal loop B of the hairpin ribozyme: implications for secondary structure," *Nucleic Acids Research* 24:573–581 (1996).

Scott et al., "The crystal structure of an All–RNA hammerhead ribozyme: A proposed mechanism for RNA catalytic cleavage," *Cell* 81:991–1002 (1995).

Strobel et al., "Minor Groove Recognition of the Conserved G·U Pair at the Tetrahymena Ribozyme Reaction Site," *Science* 267:675–679 (1995).

Sullenger and Cech, "Ribozyme–mediated repair of defective mRNA by targeted trans–splicing," *Nature* 371:619–622 (1994).

Sullenger and Cech, "Tethering Ribozymes to a Retroviral Packaging Signal for Destruction of Viral RNA," *Science* 262:1566–1569 (1993).

Szostak, "In Vitro Genes," *TIBS* 17:89–93 (1993).

Szostak, "Structure and Activity of Ribozymes," *Redesigning the Molecules of Life*, edited by Benner, Springer–Verlag Berlin Heideilberg, pp. 87–113 (1988).

Thompson et al., "Improved accumulation and activity of ribozymes expressed from a tRNA–based RNA polymerase III promoter," *Nucleic Acids Research* 23:2259–2268 (1995).

Uhlenbeck, "A Small Catalytic Oligoribonucleotide," *Nature* 328:596–600 (1987) (this is listed as Nature 327 in the various specifications, but it is actually 328).

Usman and Cedergren, "Exploiting the chemical synthesis of RNA," *TIBS* 17:334–339 (1992).

Usman and McSwiggen, "Ch. 30—Catalytic RNA (Ribozymes) as Drugs," *Annual Reports in Medicinal Chemistry* 30:285:294 (1995).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Symposium Series* 31:163–164 (1994).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994).

Wincott et al., "Synthesis, deprotection, analysis and purification of RNA and ribozymes," *Nucleic Acids Research* 23(14):2677–2684 (1995).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Yuan et al., "Targeted cleavage of mRNA by human RNase P," *Proc. Natl. Acad. Sci. USA* 89:8006–8010 (1992).

Zarrinkar and Williamson, "The P9.1–P9.2 peripheral extension helps guide folding of the Tetrahymena ribozyme," *Nucleic Acids Research* 24:854–858 (1996).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

Zimmerly et al., "A Group II Intron RNA is a Catalytic Component of a DNA Endonuclease Involved in Intron Mobility," *Cell* 83:529–538 (1995).

* cited by examiner

*Figure 1: Hammerhead Ribozyme*

Figure 2. Hammerhead Ribozyme Substrate Motifs

PRIOR ART

Figure 3: Hairpin Ribozyme

PRIOR ART

Figure 4. Hepatitis Delta Virus (HDV) Ribozyme (SEQ ID NO. 9)

PRIOR ART

Figure 5. Neurospora vs Ribozyme

PRIOR ART

Figure 7. Hammerhead Ribozyme

PRIOR ART

Figure 8. A Scheme for the Synthesis of Defined Ribozyme Libraries

Figure 9. Design and Synthesis of a Random Hammerhead Ribozyme Library (A), and Theoretical Complexities of a Random Hammerhead Library With Different Arm-Lengths (B)

Figure 10. Strategy for Discovery of Therapeutic Gene Targets Using Random Ribozyme Libraries Figure 11. Example of How Random Ribzoyme Libraries Could Be Used to Discover Critical Genes Involved in ICAM Expression Figure 12. Ribozyme Cloning Strategy: Design of Oligonucleotides Encoding Ribozyme Sequences and Preparation for Cloning

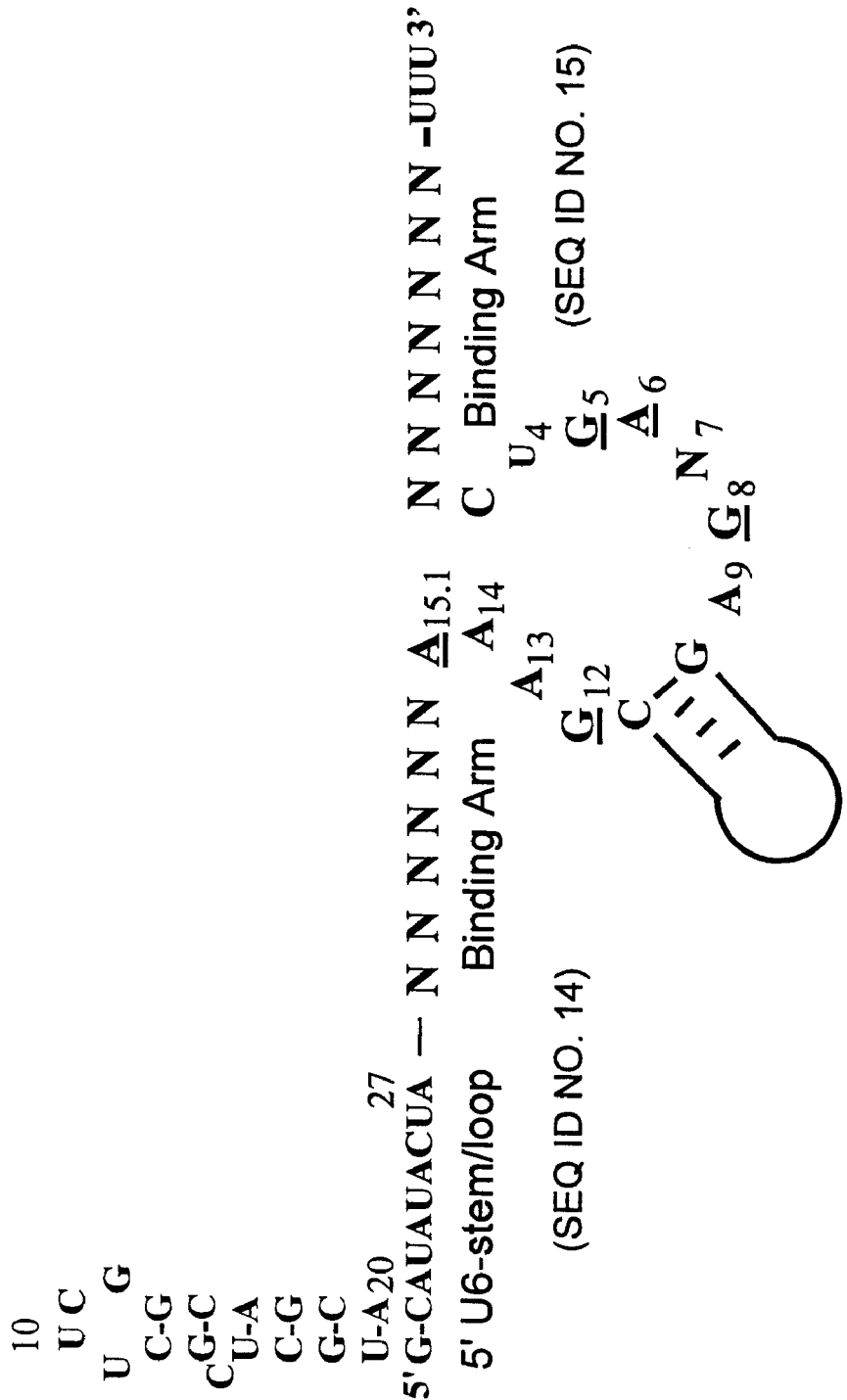
Figure 15D: U6+27 Hammerhead Ribozyme Transcription Unit

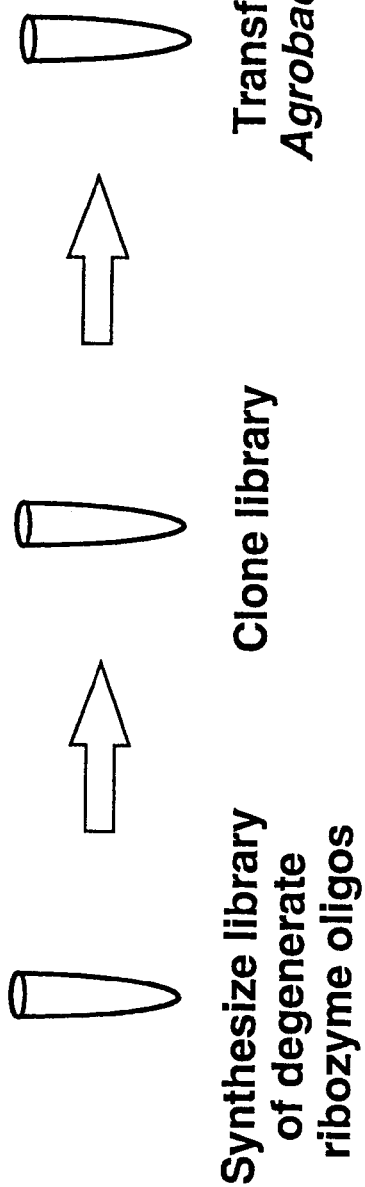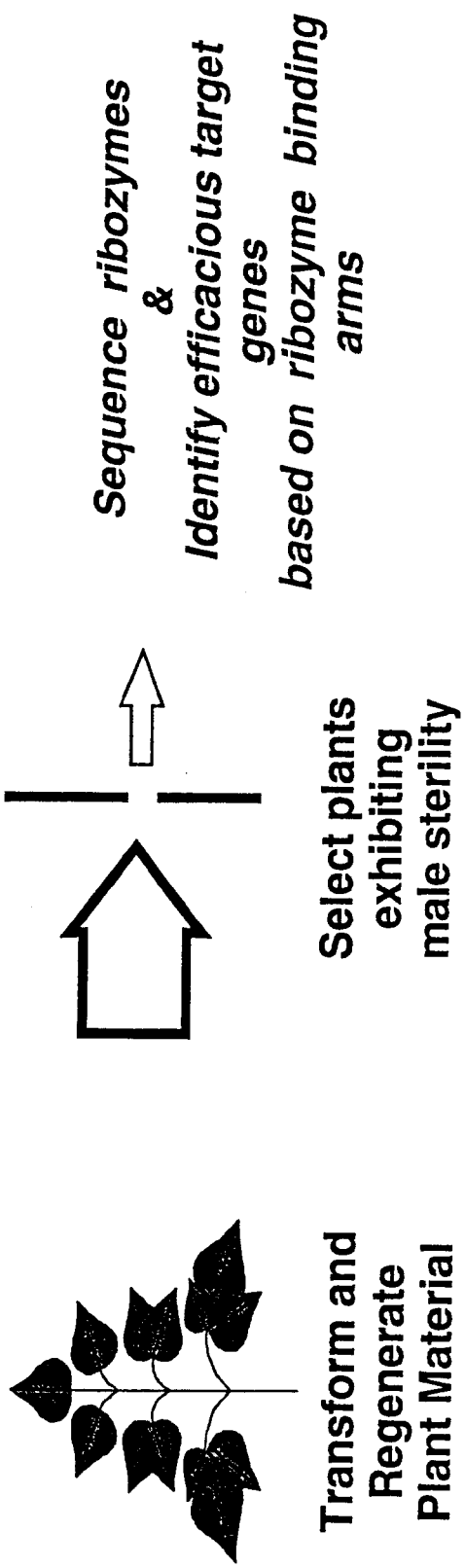
Fig. 16

Monomer and Multimer Random Library Transcripts
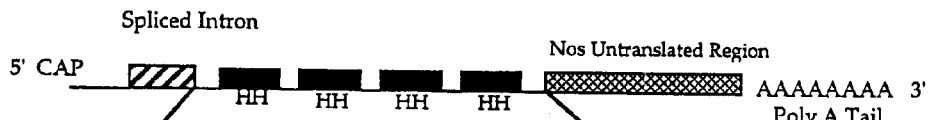
Fig. 17

SEQUENCE LISTING

<160> NUMBER OF SEQ ID NOS: 15

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Enzymatic
      Nucleic Acid

<400> SEQUENCE: 1
tttcggccta acggcctcat cag                                          23

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Enzymatic
      Nucleic Acid

<400> SEQUENCE: 2
cgaaatcaat tg                                                12

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Enzymatic
      Nucleic Acid

<400> SEQUENCE: 3
cgtacgacac gaaagtatcg                                        20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Enzymatic
      Nucleic Acid

<400> SEQUENCE: 4
ctgatgaggc cgaggccgaa a                                      21

<210> SEQ ID NO 5
<211> LENGTH: 11
<212> TYPE: DNA
<213> ORGANISM: Homo sapiens
<220> FEATURE:
<221> NAME/KEY: misc_feature
<222> LOCATION: (1)..(4)
<223> OTHER INFORMATION: n stands for any a, c, g, or u
<221> NAME/KEY: misc_feature
<222> LOCATION: (7)..(11)
<223> OTHER INFORMATION: n stands for any a, c, g, or u

<400> SEQUENCE: 5
nnnnuhnnnn n                                                 11

<210> SEQ ID NO 6
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(5)
<223> OTHER INFORMATION: n stands for any a, c, g, or u
<221> NAME/KEY: misc_feature
<222> LOCATION: (10)..(10)
<223> OTHER INFORMATION: n stands for any a, c, g, or u
<221> NAME/KEY: misc_feature
<222> LOCATION: (14)..(19)
<223> OTHER INFORMATION: n stands for any a, c, g, or u
<221> NAME/KEY: misc_feature
<222> LOCATION: (25)..(28)
<223> OTHER INFORMATION: n stands for any a, c, g, or u

<400> SEQUENCE: 6
nnnnncugan gagnnnnnnc gaaannnn                               28

<210> SEQ ID NO 7
<211> LENGTH: 15
<212> TYPE: RNA
<213> ORGANISM: Homo sapiens
<220> FEATURE:
<221> NAME/KEY: misc_feature
<222> LOCATION: (1)..(7)

```
<223> OTHER INFORMATION: n stands for any a, c, g, or u
<221> NAME/KEY: misc_feature
<222> LOCATION: (9)..(9)
<223> OTHER INFORMATION: n stands for any a, c, g, or u
<221> NAME/KEY: misc_feature
<222> LOCATION: (13)..(15)
<223> OTHER INFORMATION: n stands for any a, c, g, or u
<221> NAME/KEY: misc_feature
<222> LOCATION: (1)..(9)
<223> OTHER INFORMATION: 2'-O-Methyl
<221> NAME/KEY: misc_feature
<222> LOCATION: (12)..(12)
<223> OTHER INFORMATION: 2'-O-Methyl
<221> NAME/KEY: misc_feature
<222> LOCATION: (14)..(15)
<223> OTHER INFORMATION: 2'-O-Methyl
<221> NAME/KEY: misc_feature
<222> LOCATION: (1)..(1)
<223> OTHER INFORMATION: 2'-O-Methyl
<221> NAME/KEY: misc_feature
<222> LOCATION: (3)..(4)
<223> OTHER INFORMATION: 2'-O-Methyl
<221> NAME/KEY: misc_feature
<222> LOCATION: (6)..(11)
<223> OTHER INFORMATION: 2'-O-Methyl

<400> SEQUENCE: 7
nnnnnnnyng hynnn                                              15

<210> SEQ ID NO 8
<211> LENGTH: 47
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(4)
<223> OTHER INFORMATION: n stands for any a, c, g, or u
<221> NAME/KEY: misc_feature
<222> LOCATION: (9)..(19)
<223> OTHER INFORMATION: n stands for any a, c, g, or u
<221> NAME/KEY: misc_feature
<222> LOCATION: (25)..(31)
<223> OTHER INFORMATION: n stands for any a, c, g, or u
<221> NAME/KEY: misc_feature
<222> LOCATION: (39)..(47)
<223> OTHER INFORMATION: n stands for any a, c, g, or u

<400> SEQUENCE: 8
nnnngaagnn nnnnnnnnna aahannnnnn nacauuacnn nnnnnn            47

<210> SEQ ID NO 9
<211> LENGTH: 49
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (18)..(24)
<223> OTHER INFORMATION: n stands for any a, c, g, or u

<400> SEQUENCE: 9
cuccaccucc ucgcggunnn nnnngggcua cuucgguagg cuaagggag         49

<210> SEQ ID NO 10
<211> LENGTH: 176
<212> TYPE: RNA
<213> ORGANISM: Homo sapiens

<400> SEQUENCE: 10
```
gggaaagcuu gcgaagggcg ucgucgcccc gagcgguagu aagcagggaa cucaccucca    60
auuucaguac ugaaauuguc guagcaguug acuacuguua ugugauuggu agaggcuaag   120
ugacgguauu ggcguaaguc aguauugcag cacagcacaa gcccgcuugc gagaau       176

<210> SEQ ID NO 11
<211> LENGTH: 18
<212> TYPE: DNA
<213> ORGANISM: Homo sapiens
<220> FEATURE:
<221> NAME/KEY: misc_feature
<222> LOCATION: (3)..(6)
<223> OTHER INFORMATION: n stands for any a, c, g, or u
<221> NAME/KEY: misc_feature
<222> LOCATION: (9)..(13)
<223> OTHER INFORMATION: n stands for any a, c, g, or u

<400> SEQUENCE: 11
ggnnnnuhnn nnnaaaaa                                                  18

<210> SEQ ID NO 12
<211> LENGTH: 15
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(7)
<223> OTHER INFORMATION: n stands for any a, c, g, or u
<221> NAME/KEY: misc_feature
<222> LOCATION: (12)..(12)
<223> OTHER INFORMATION: n stands for any a, c, g, or u

<400> SEQUENCE: 12
nnnnnnncug angag                                                     15

<210> SEQ ID NO 13
<211> LENGTH: 11
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (6)..(11)
<223> OTHER INFORMATION: n stands for any a, c, g, or u

<400> SEQUENCE: 13
cgaaannnnn n                                                         11

<210> SEQ ID NO 14
<211> LENGTH: 38
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(33)
<223> OTHER INFORMATION: 2'-O-Methyl
<221> NAME/KEY: misc_feature
<222> LOCATION: (35)..(36)
<223> OTHER INFORMATION: 2'-O-Methyl
<221> NAME/KEY: misc_feature
<222> LOCATION: (38)..(38)
<223> OTHER INFORMATION: 2'-O-Methyl
<221> NAME/KEY: misc_feature
<222> LOCATION: (28)..(33)
<223> OTHER INFORMATION: n stands for any a, c, g, or u -continued

```
<400> SEQUENCE: 14
gugcucgcuu cggcagcaca uauacuannn nnnaaagc                              38

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(2)
<223> OTHER INFORMATION: 2'-O-Methyl
<221> NAME/KEY: misc_feature
<222> LOCATION: (4)..(4)
<223> OTHER INFORMATION: 2'-O-Methyl
<221> NAME/KEY: misc_feature
<222> LOCATION: (7)..(18)
<223> OTHER INFORMATION: 2'-O-Methyl
<221> NAME/KEY: misc_feature
<222> LOCATION: (4)..(4)
<223> OTHER INFORMATION: n stands for any a, c, g, or u
<221> NAME/KEY: misc_feature
<222> LOCATION: (9)..(15)
<223> OTHER INFORMATION: n stands for any a, c, g, or u

<400> SEQUENCE: 15
gagnagucnn nnnnnuuu                                                    18
```

METHOD FOR TARGET SITE SELECTION AND DISCOVERY

This patent application is a continuation of Thompson, U.S. Ser. No. 09/112,086, filed Jul. 8, 1998, issued as U.S. Pat. No. 6,183,959, which is a continuation-in-part of Thompson, U.S. Ser. No. 09/108,087, filed Jun. 30, 1998, abandoned, which is a utility application of Thompson, U.S. Ser. No. 60/051,718, filed Jul. 3, 1997, all entitled "METHOD FOR TARGET SITE SELECTION AND DISCOVERY" and all hereby incorporated by reference herein including drawings.

BACKGROUND OF THE INVENTION

This invention relates to methods of designing and isolating of nucleic acid molecules with desired catalytic activity, the molecules themselves and derivatives thereof.

The following is a brief description of catalytic nucleic acid molecules. This summary is not meant to be complete but is provided only for understanding of the invention that follows. This summary is not an admission that all of the work described below is prior art to the claimed invention.

Catalytic nucleic acid molecules (ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target cleavage of virtually any RNA transcript (Zaug et al., 324, *Nature* 429 1986; Cech, 260 *JAMA* 3030, 1988; and Jefferies et al., 17 *Nucleic Acids Research* 1371, 1989). Catalytic nucleic acid molecules mean any nucleotide base-comprising molecule having the ability to repeatedly act on one or more types of molecules, including but not limited to enzymatic nucleic acid molecules. By way of example but not limitation, such molecules include those that are able to repeatedly cleave nucleic acid molecules, peptides, or other polymers, and those that are able to cause the polymerization of such nucleic acids and other polymers. Specifically, such molecules include ribozymes, DNAzymes, external guide sequences and the like. It is expected that such molecules will also include modified nucleotides compared to standard nucleotides found in DNA and RNA.

Because of their sequence-specificity, trans-cleaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited. In addition, enzymatic nucleic acid molecules can be used to validate a therapeutic gene target and/or to determine the function of a gene in a biological system (Christoffersen, 1997, *Nature Biotech.* 15, 483).

There are at least seven basic varieties of enzymatic RNA molecules derived from naturally occurring self-cleaving RNAs (see Table I). Each can catalyze the hydrolysis of RNA phosphodiester bonds in trans (and thus can cleave other RNA molecules) under physiological conditions. In general, enzymatic nucleic acids act by first binding to a substrate/target RNA. Such binding occurs through the substrate/target binding portion of an enzymatic nucleic acid molecule which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic and selective cleavage of such a target RNA will destroy its ability to direct synthesis of an encoded protein. After an enzymatic nucleic acid has bound and cleaved its RNA target, it is released from that RNA to search for another target and thus can repeatedly bind and cleave new targets.

In addition, several in vitro selection (evolution) strategies (Orgel, 1979, *Proc. R. Soc. London*, B 205, 435) have been used to evolve new nucleic acid catalysts capable of catalyzing a variety of reactions, such as cleavage and ligation of phosphodiester linkages and amide linkages, (Joyce, 1989, *Gene*, 82, 83–87; Beaudry et al, 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J.*, 9, 1183; Breaker, 1996, *Curr. Op. Biotech.*, 7, 442; Breaker, 1997, *Nature Biotech.* 15, 427).

There are several reports that describe the use of a variety of in vitro and in vivo selection strategies to study structure and function of catalytic nucleic acid molecules (Campbell et al., 1995, *RNA* 1, 598; Joyce 1989, *Gene*, 82,83; Lieber et al., 1995, *Mol Cell Biol.* 15, 540; Lieber et al, International PCT Publication No. WO 96/01314; Szostak 1988, in *Redesigning the Molecules of Life*, Ed. S. A. Benner, pp 87, Springer-Verlag, Germany; Kramer et al., U.S. Pat. No. 5,616,459; Draper et al., U.S. Pat. No. 5,496,698; Joyce, U.S. Pat. No. 5,595,873; Szostak et al., U.S. Pat. No. 5,631,146).

The enzymatic nature of a ribozyme is advantageous over other technologies, since the effective concentration of ribozyme sufficient to effect a therapeutic treatment is generally lower than that of an antisense oligonucleotide. This advantage reflects the ability of the ribozyme to act enzymatically. Thus, a single ribozyme (enzymatic nucleic acid) molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

The development of ribozymes that are optimal for catalytic activity would contribute significantly to any strategy that employs RNA-cleaving ribozymes for the purpose of regulating gene expression. The hammerhead ribozyme, for example, functions with a catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) can be 10- to 100-fold slower. In contrast, the RNase P holoenzyme can catalyze pre-tRNA cleavage with a $k_{cat}$ of ~30 min$^-$ under optimal assay conditions. An artificial 'RNA ligase' ribozyme (Bartel et al., supra) has been shown to catalyze the corresponding self-modification reaction with a rate of ~100 min$^{-1}$. In addition, it is known that certain modified hammerhead ribozymes that have substrate binding arms made of DNA catalyze RNA cleavage with multiple turn-over rates that approach 100 min$^{-1}$. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain self-cleaving ribozymes may not be optimized to give maximal catalytic activity, or that entirely new RNA motifs could be made that display significantly faster rates for RNA phosphoester cleavage.

An extensive array of site-directed mutagenesis studies have been conducted with ribozymes such as the hammerhead, hairpin, hepatitis delta virus, group L group II and others, to probe relationships between nucleotide sequence, chemical composition and catalytic activity. These systematic studies have made clear that most nucleotides in the conserved core of these ribozymes cannot be mutated without significant loss of catalytic activity. In contrast, a combinatorial strategy that simultaneously screens a large pool of mutagenized ribozymes for RNAs that retain catalytic activity could be used more efficiently to define immutable sequences and to identify new ribozyme variants.

Certain strategies to optimize reagents, such as the ribozymes, to down regulate the expression of a known target sequence have recently been reported:

Kramer et al., U.S. Pat. No. 5,616,459, describe a selection method for optimizing a hammerhead or a hairpin ribozyme by mutagenizing the "catalytic domain" of these ribozymes while keeping the binding arm sequence constant. Hammerhead or hairpin ribozymes optimal for cleaving a specific known target site are selected.

Roninson et al., U.S. Pat. No. 5,217,889, and Draper et al., U.S. Pat. No. 5,496,698, describe a method for selecting ribozymes capable of cleaving a known target sequence by fragmenting the DNA of the target gene, inserting the catalytic core of a known ribozyme into these DNA fragments, cloning these fragments into a vector, expressing these ribozymes in a cell and selecting for the vector encoding the optimal ribozyme.

Draper et al., U.S. Pat. No. 5,496,698, also describes a method for identifying ribozyme cleavage sites in a known RNA target by using ribozymes with randomized binding arms. Draper states on column 2, third full paragraph:

"Applicant provides an in vivo system for selection of ribozymes targeted to a defined RNA target The system allows many steps in a selection process for desired ribozymes to be bypassed. In this system, a population of ribozymes having different substrate binding arms (and thus active at different RNA sequences) is introduced into a population of cells including a target RNA molecule. The cells are designed such that only those cells which include a useful ribozyme will survive, or only those cells including a useful ribozyme will provide a detectable signal. In this way, a large population of randomly or non-randomly formed ribozyme molecules may be tested in an environment which is close to the true environment in which the ribozyme might be utilized as a therapeutic agent." (Emphasis added)

Leiber et al., supra, describes a method for screening a known target RNA for accessible ribozyme cleavage sites. This method involves the incubation of a library of hammerhead ribozymes, with randomized binding arms, with the target RNA in vitro and identification of hammerhead ribozymes that cleave the target RNA. The selected ribozymes are then introduced into a cell to test their activity.

The references cited above are distinct from the presently claimed invention since they do not disclose and/or contemplate the nucleic acid molecules and the methods for target site selection and discovery of the instant invention.

SUMMARY OF THE INVENTION

This invention relates to nucleic acid molecules with catalytic activity, that are particularly useful for cleavage of RNA or DNA. This invention also relates to a method for using nucleic acid catalysts to identify accessible target sites in a cell, to evaluate gene function, to validate a gene target for therapeutic intervention, and to identify and isolate nucleic acid molecules such as genes, involved in a biological process.

In a first aspect the invention features a method for identifying one or more nucleic acid molecules, such as gene(s), involved in a process (such as, cell growth, proliferation, apoptosis, morphology, angiogenesis, differentiation, migration, viral multiplication, drug resistance, signal transduction, cell cycle regulation, temperature sensitivity, chemical sensitivity and others) in a biological system, such as a cell. The method involves the steps of: a) providing a random library of nucleic acid catalysts, with a substrate binding domain and a catalytic domain, where the substrate binding domain has a random sequence, to the biological system under conditions suitable for the process to be altered; b) identifying any nucleic acid catalyst present in that biological system where the process has been altered by any nucleic acid catalyst; and c) determining the nucleotide. sequence of at least a portion of the binding arm of such a nucleic acid catalyst to allow identification of the nucleic acid molecule involved in the process in that biological system.

In a related aspect the invention features a method for identification of a nucleic acid molecule capable of modulating a process in a biological system. The method includes: a) introducing a library of nucleic acid catalysts with a substrate binding domain and a catalytic domain, where the substrate binding domain has a random sequence, into the biological system under conditions suitable for modulating the process; and b) determining the nucleotide sequence of at least a portion of the substrate binding domain of any nucleic acid catalyst from a biological system where the process has been modulated to allow said identification of the nucleic acid molecule capable of modulating said process in that biological system.

In a second aspect, the invention the invention further concerns a method for identification of a nucleic acid catalyst capable of modulating a process in a biological system. This involves: a) introducing a library of nucleic acid catalysts with a substrate binding domain and a catalytic domain, where the substrate binding domain has a random sequence, into the biological system under conditions suitable for modulating the process; and b) identifying any nucleic acid catalyst from a biological system where the process has been modulated.

By "nucleic acid catalyst" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner.

Such a molecule with endonuclease activity may have complementarity in a substrate binding region to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule.

By "enzymatic portion" or "catalytic domain" is meant that portion/region of the ribozyme essential for cleavage of a nucleic acid substrate (for example see FIG. 7).

By "substrate binding arm" or "substrate binding domain" is meant that portion/region of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–4. That is, these arms contain sequences within a ribozyme which are intended to bring ribozyme and target together through complementary base-pairing interactions. The ribozyme of the invention may have binding arms that are contiguous or non-contiguous and may be varying lengths. The length of the binding arm(s) are preferably greater than or equal to four nucleotides; specifically 12–100 nucleotides; more specifically 14–24 nucleotides long. If a ribozyme with two binding arms are chosen, then the length of the binding aims are symmetrical (i.e., each of the binding arms is of the same length; e.g. six and six nucleotides or seven and seven nucleotides long) or asymmetrical (i.e., the binding arms are of different length; e.g., six and three nucleotides or three and six nucleotides long).

By "nucleic acid molecule" as used herein is meant a molecule having nucleotides. The nucleic acid can be single, double or multiple stranded and may comprise modified or unmodified nucleotides or non-nucleotides or various mixtures and combinations thereof. An example of a nucleic acid molecule according to the invention is a gene which encodes for macromolecule such as a protein.

By "complementarity" as used herein is meant a nucleic acid that can form hydrogen bond(s) with other nucleic acid sequence by either traditional Watson-Crick or other non-traditional types (for example, Hoogsteen type) of base-paired interactions.

The "biological system" as used herein may be a eukaryotic system or a prokaryotic system, may be a bacterial cell, plant cell or a mammalian cell, or may be of plant origin, mammalian origin, yeast origin, Drosophila origin, or archebacterial origin.

Other features and advantages of the invention will be apparent from the following description of the preferred embodiments thereof, and from the claims.

DESCRIPTION OF THE PREFERRED EMBODIMENTS

The drawings will first briefly be described.

Drawings:

FIG. 1 is a diagrammatic representation of the hammerhead ribozyme domain known in the art. Stem II can be 2 base-pair long. Each N is independently any base or non-nucleotide as used herein; the stem I and stem III can be of any length; and the stems can be symmetric or asymmetric.

Figure 2:
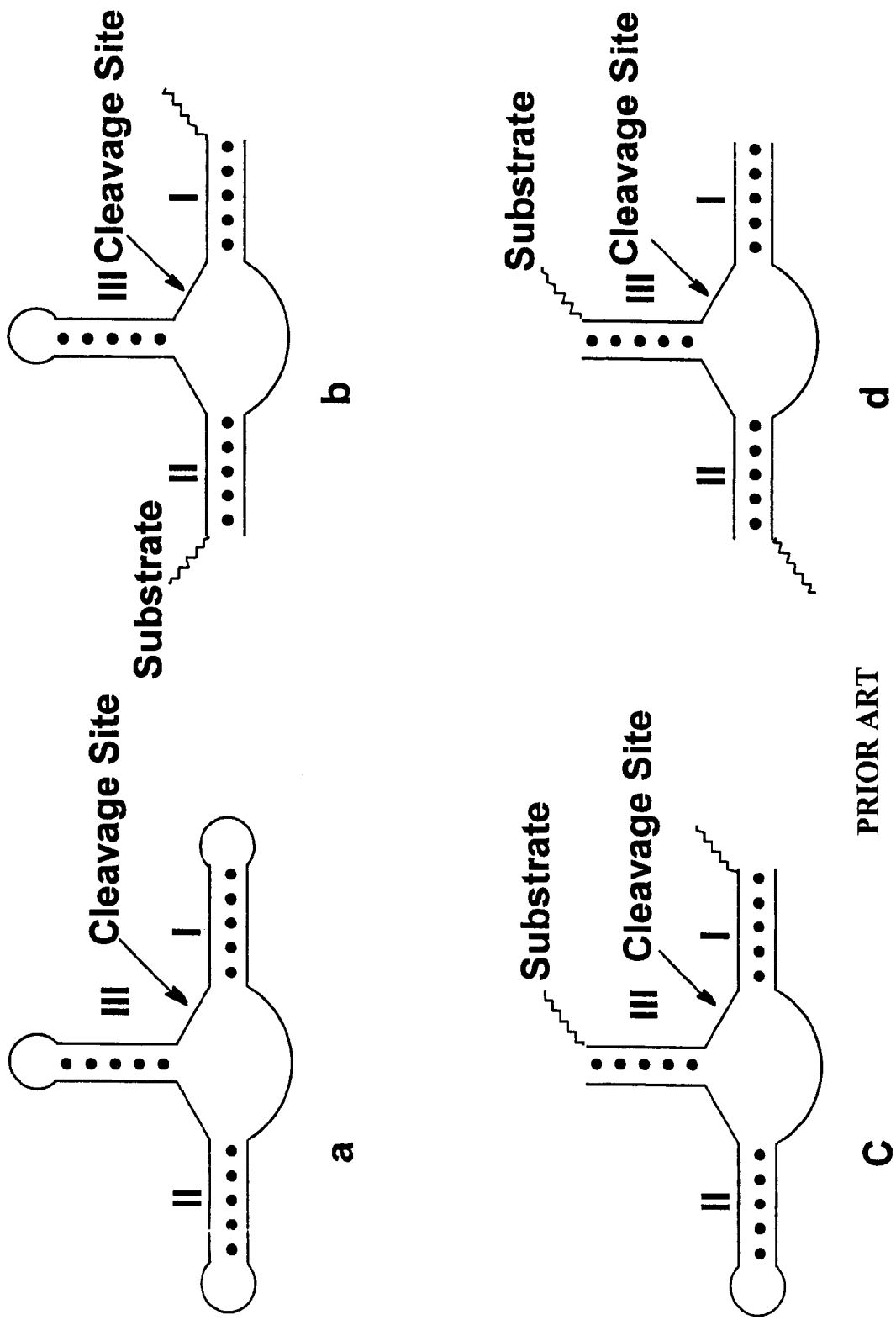
FIG. 2A is a diagrammatic representation of the hammerhead ribozyme domain known in the art.
FIG. 2B is a diagrammatic representation of the hammerhead ribozyme as divided by Uhlenbeck (1987, Nature, 327, 596–600) into a substrate and enzyme portion.

FIG. 2C is a similar diagram showing the hammerhead divided by Haseloff and Gerlach (1988, Nature, 334, 585–591) into two portions; and FIG. 2D is a similar diagram showing the hammerhead divided by Jeffries and Symons (1989, Nucl. Acids. Res., 17, 1371–1371) into two portions.

Figure 3:
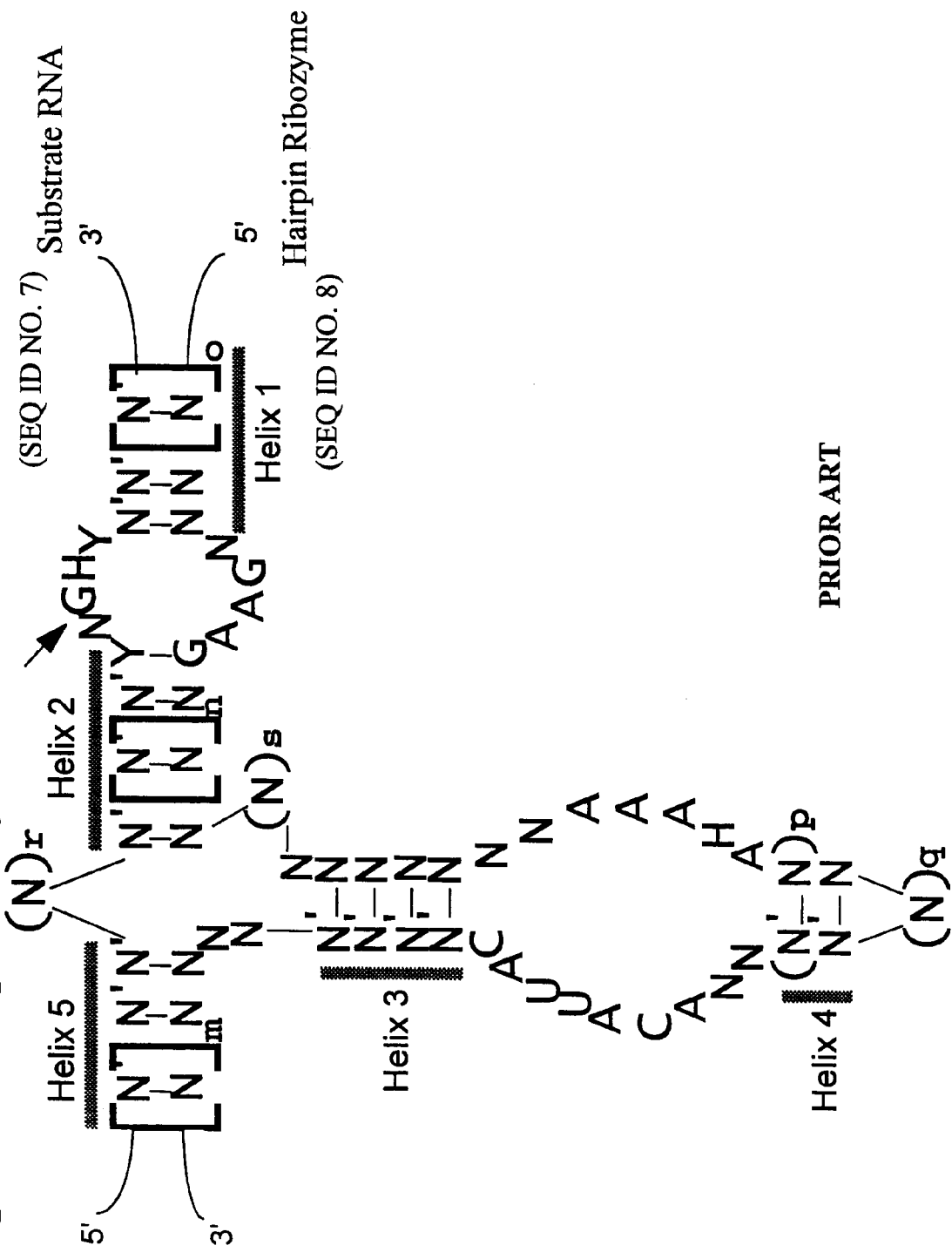

FIG. 3 is a diagrammatic representation of the general structure of a hairpin ribozyme. Helix 2 (H2) is provided with a least 4 base pairs (ie., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is 1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is 2 bases. The connecting loop can also be replaced with a non-nucleotide linker molecule. H refers to bases A, U, or C. Y refers to pyrimidine bases. "—" refers to a covalent bond.

Figure 4:
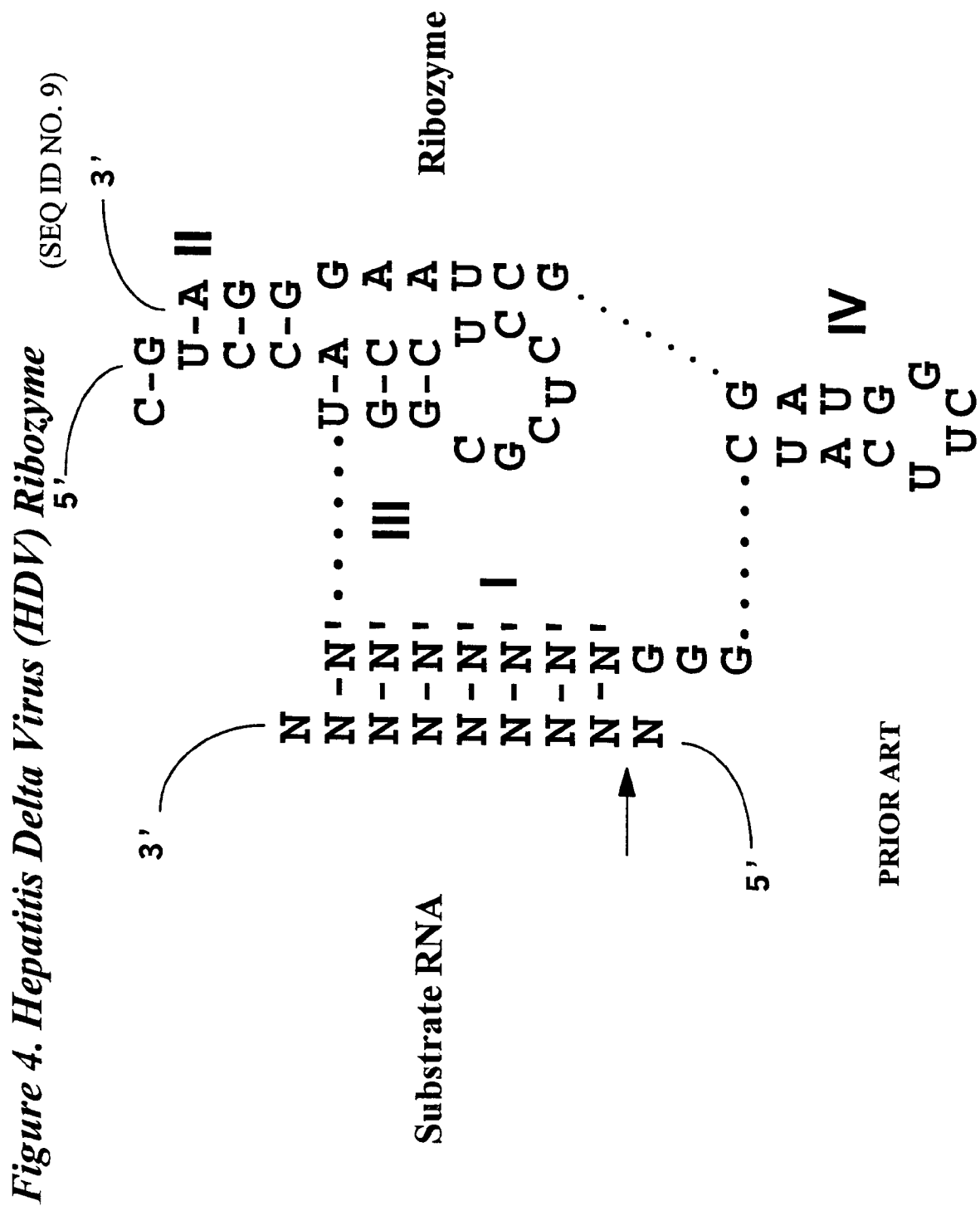

FIG. 4 is a representation of the general structure of the hepatitis delta virus ribozyme domain known in the art. In each instance, each N and N' independently is any normal or modified base and each dash represents a potential base-pairing interaction. These nucleotides may be modified at the sugar, base or phosphate.

Figure 5:
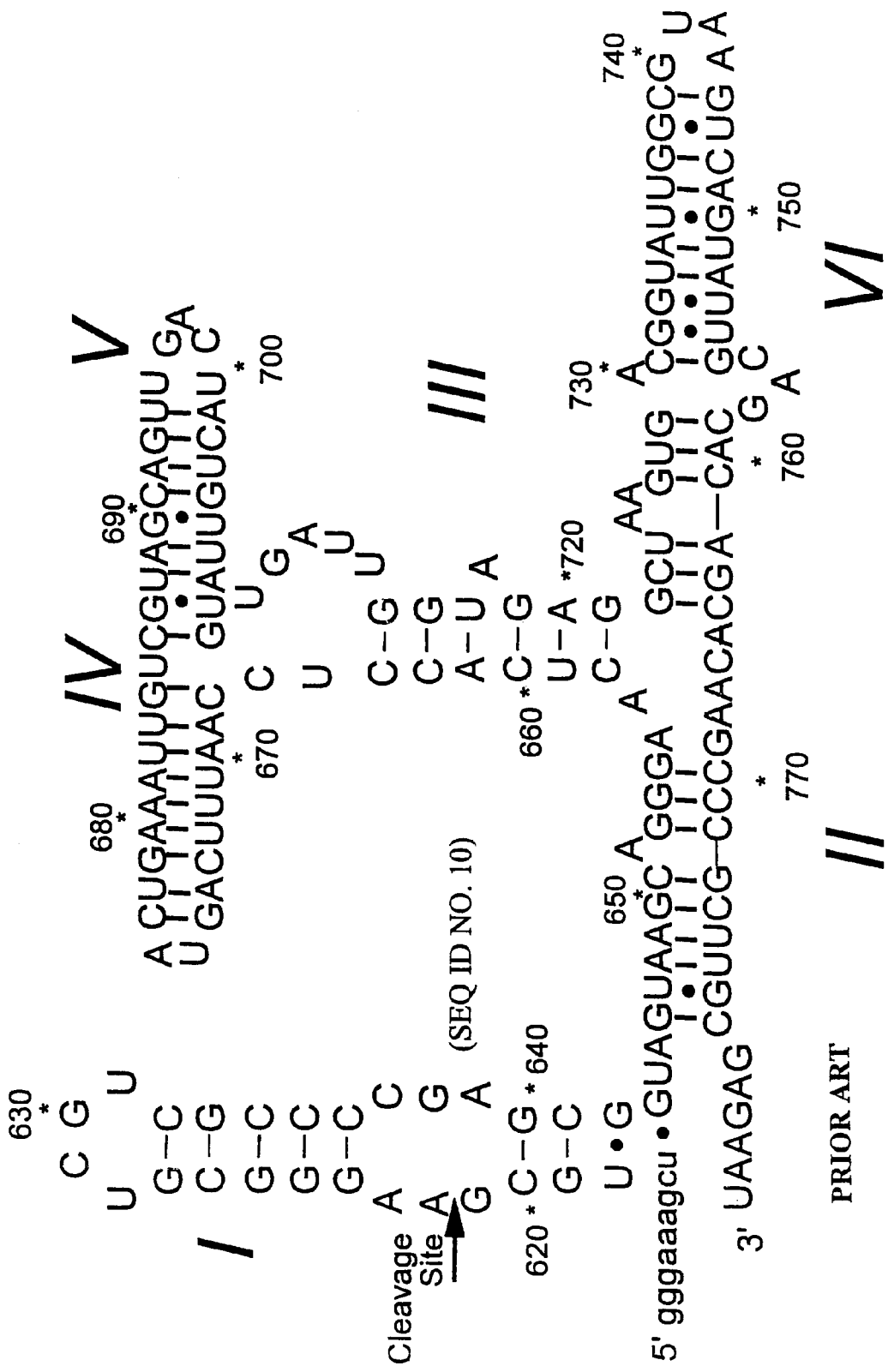

FIG. 5 is a representation of the general structure of the self-cleaving VS RNA ribozyme domain.

Figure 6:
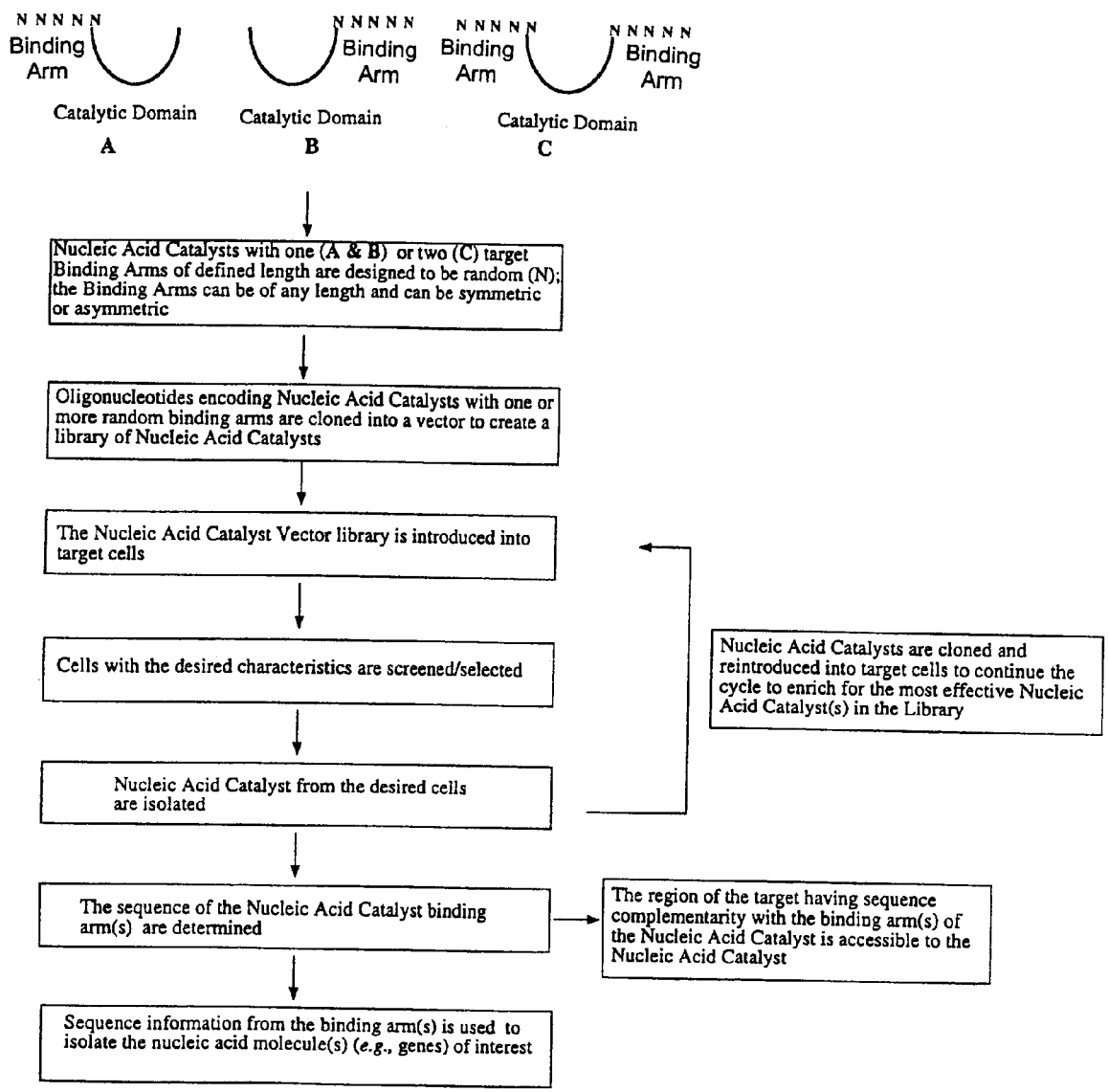

FIG. 6 shows a general approach to accessible site and target discovery using nucleic acid catalysts.

Figure 7:
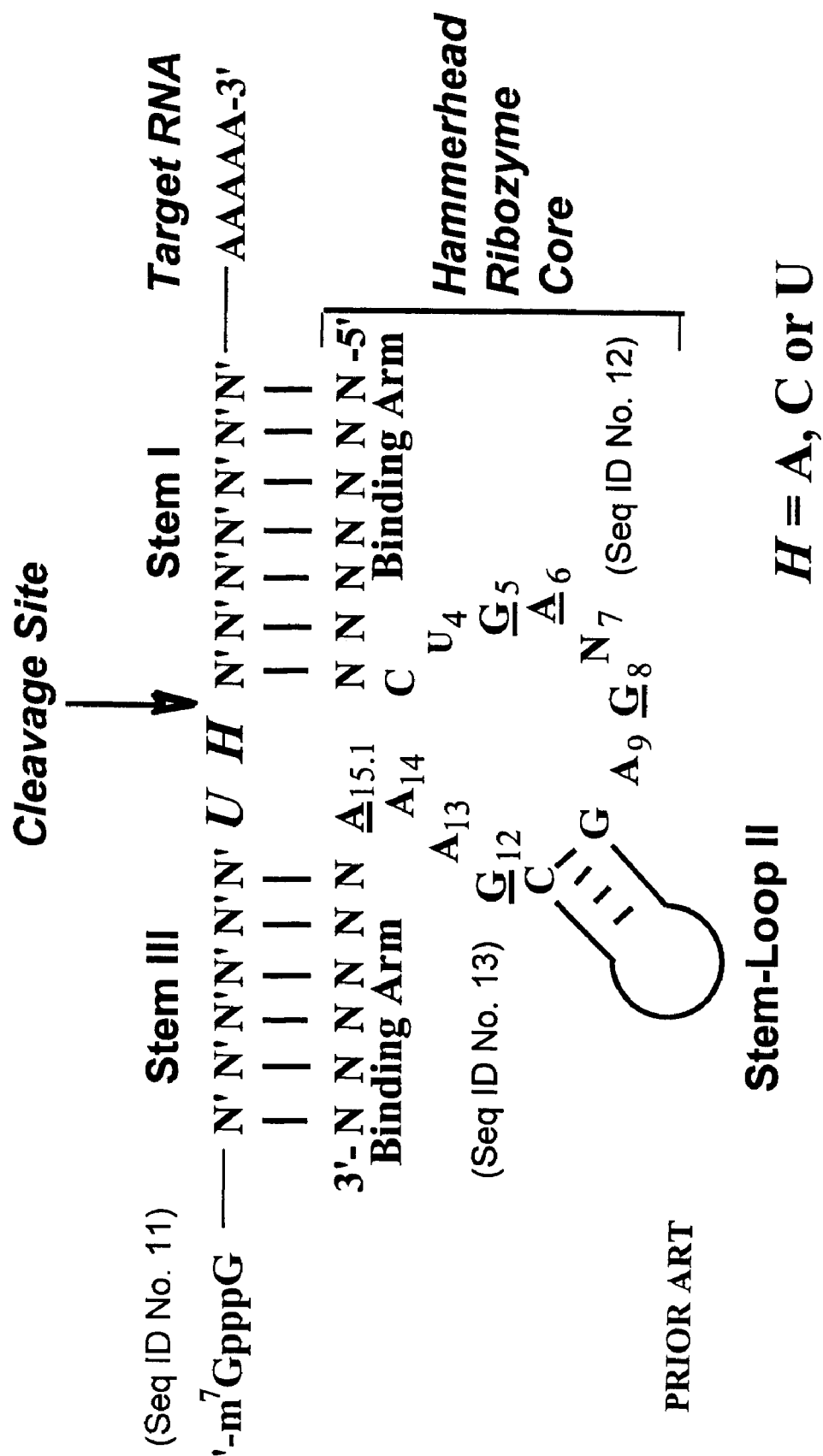

FIG. 7 is a diagram of a hammerhead ribozyme. The consensus hammerhead cleavage site in a target RNA is a "U" followed by "H" (anything but "G"). The hammerhead ribozyme cleaves after the "H". This simple di-nucleotide sequence occurs, on average, every 5 nt in a target RNA Thus, there are approximately 400 potential hammerhead cleavage sites in a 2-Kb MRNA. Stems I and II are formed by hybridization of the hammerhead binding arms with the complementary sequence in target RNA; it is these binding arms that confer specificity to the hammerhead ribozyme for its target. The binding aims of the hammerhead are interrupted by the catalytic domain that forms part of the structure responsible for cleavage.

Figure 8:
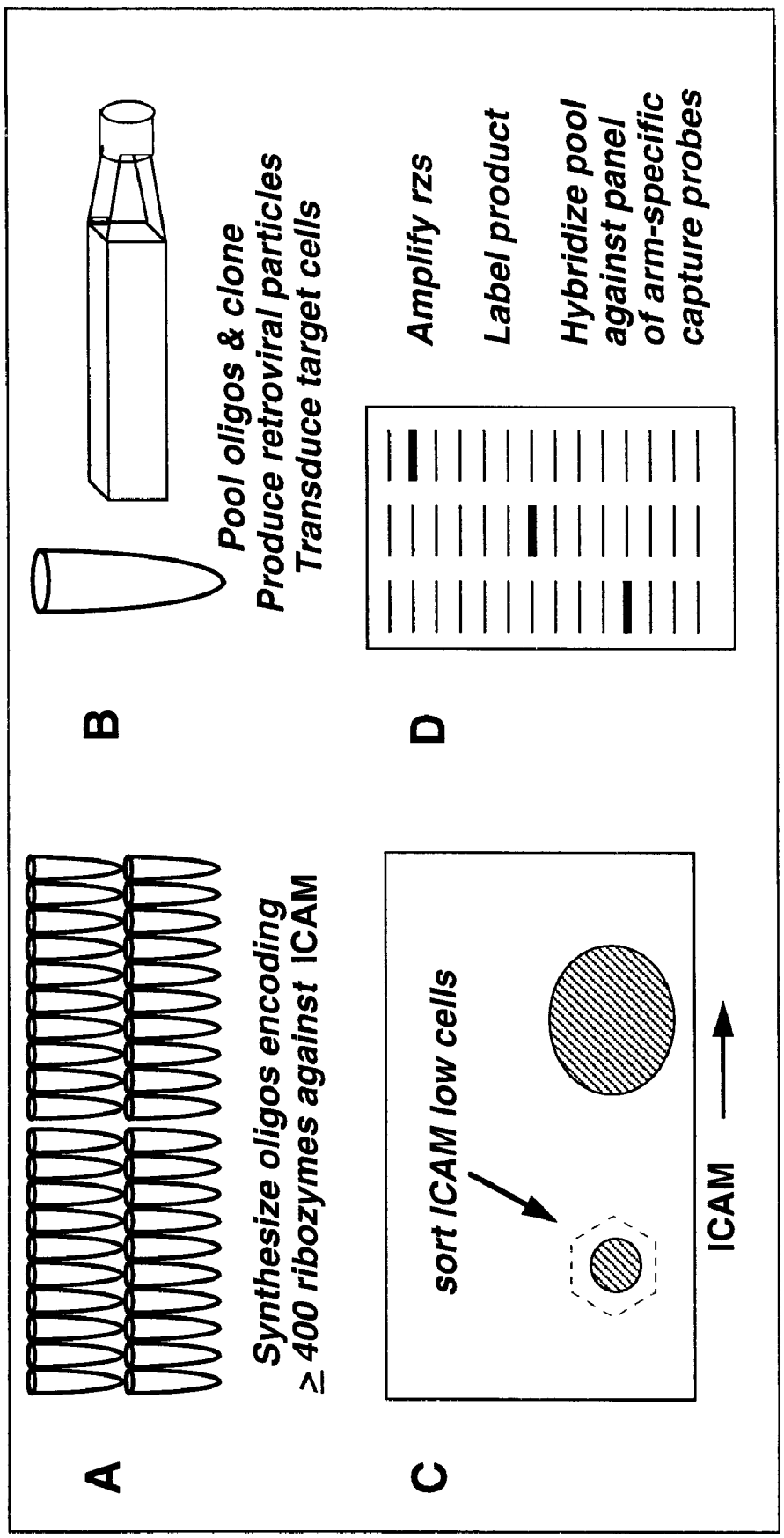

FIG. 8 shows a scheme for the design and synthesis of a Defined Library: simultaneous screen of 400 different ICAM-targeted ribozymes is used as an example. DNA oligonucleotides encoding each ICAM-targeted ribozyme are synthesized individually (A), pooled (B), then cloned and converted to retroviral vectors as a pool. The resulting retroviral vector particles are used to transduce a target cell line that expresses ICAM (B). Cells expressing ribozymes that inhibit ICAM expression (ICAM-low) are sorted from cells expressing ineffective ribozymes by FACS sorting (C), effective ribozymes enriched in the ICAM-low population of cells are identified by filter hybridization (D).

Figure 9:
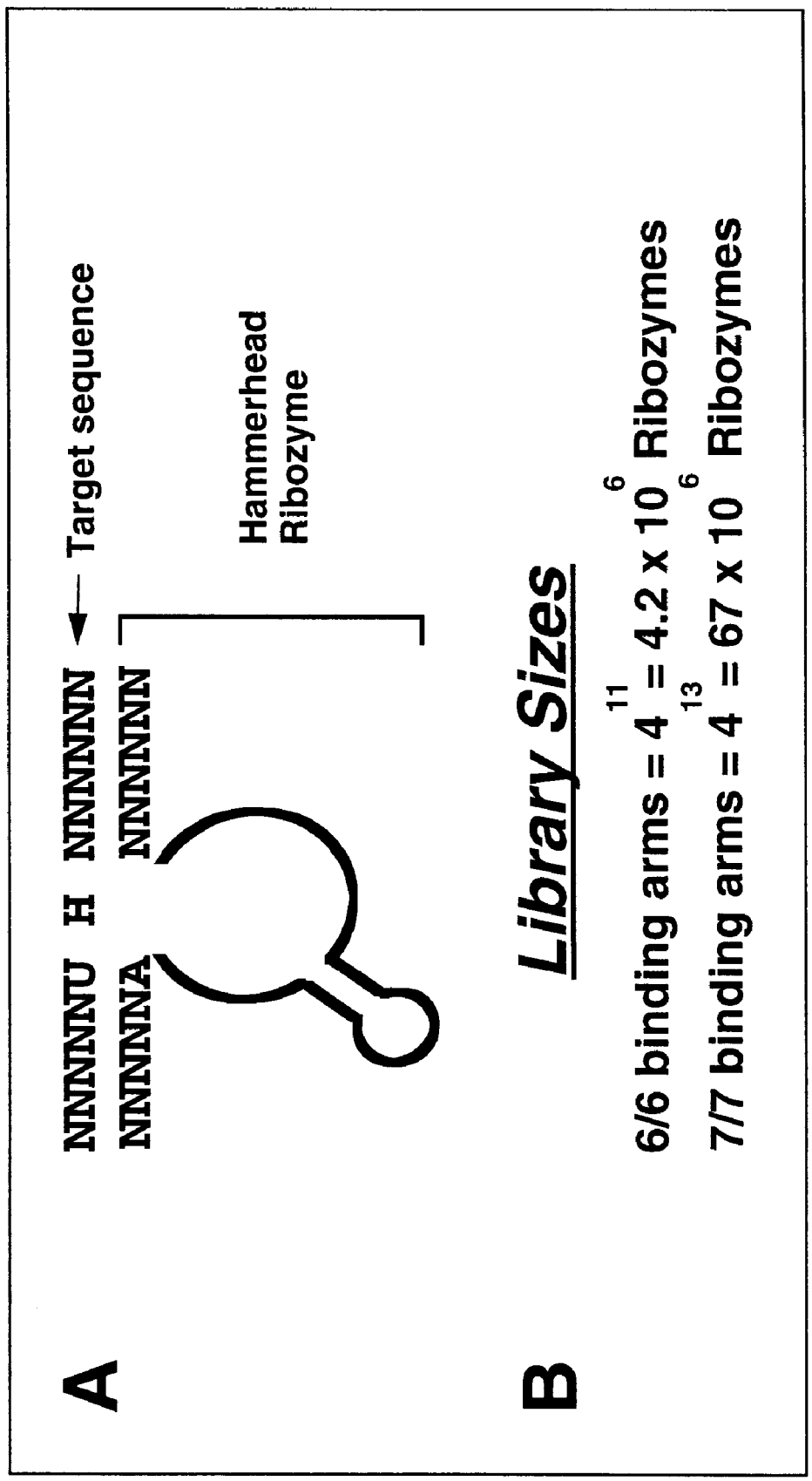

FIG. 9A shows randomization of the binding arms of a hammerhead ribozyme to produce a Random Library. The binding arms can be of any length and any symmetry, i.e., symmetrical or assymmetrical. 9B shows complexities of hammerhead Random Ribozyme Libraries comprising a 6-nt or a 7-nt long binding arms.

Figure 10:
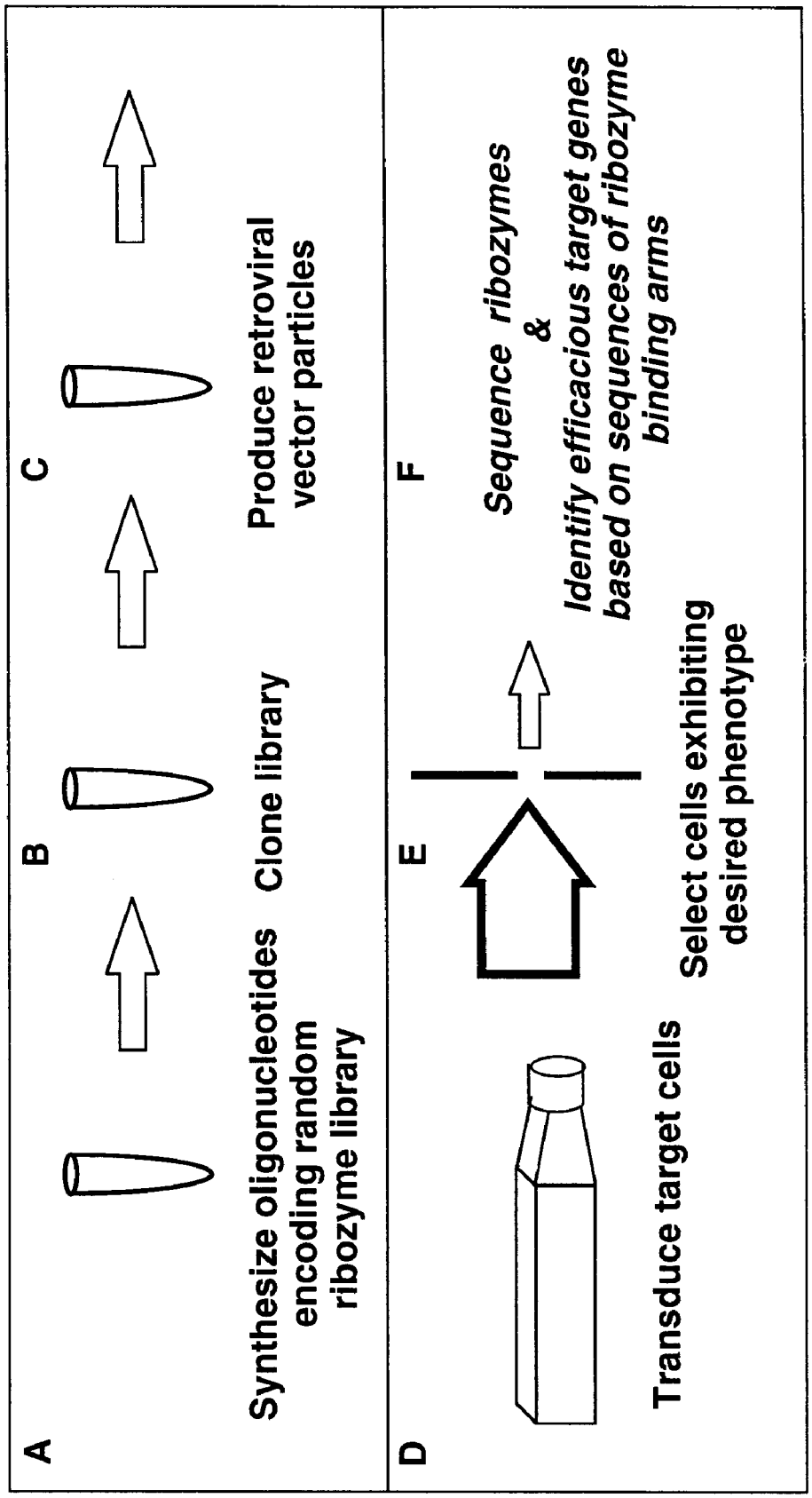

FIG. 10 is a schematic overview of Target Discovery strategy. An oligonucleotide is prepared in a single reaction vessel in which all 4 standard nucleotides are incorporated. in a random fashion in the target binding arm(s) of the ribozyme to produce a pool of all possible ribozymes (A). This pool is cloned into an appropriate vector in a single tube to produce the Random Library expression vector (B) and retroviral vector particles are produced from this pool in a single tube (C). The resulting Random Ribozyme Library retroviral expression vector pool is then used to transduce a cell type of interest (D). Cells exhibiting the desired phenotype are then separated from the rest of the population using a number of possible selection strategies (E and see text). Genes that are critical for expression of the selected phenotype can then be identified by sequencing the target binding arms of ribozymes contained in the selected population (F).

Figure 11:
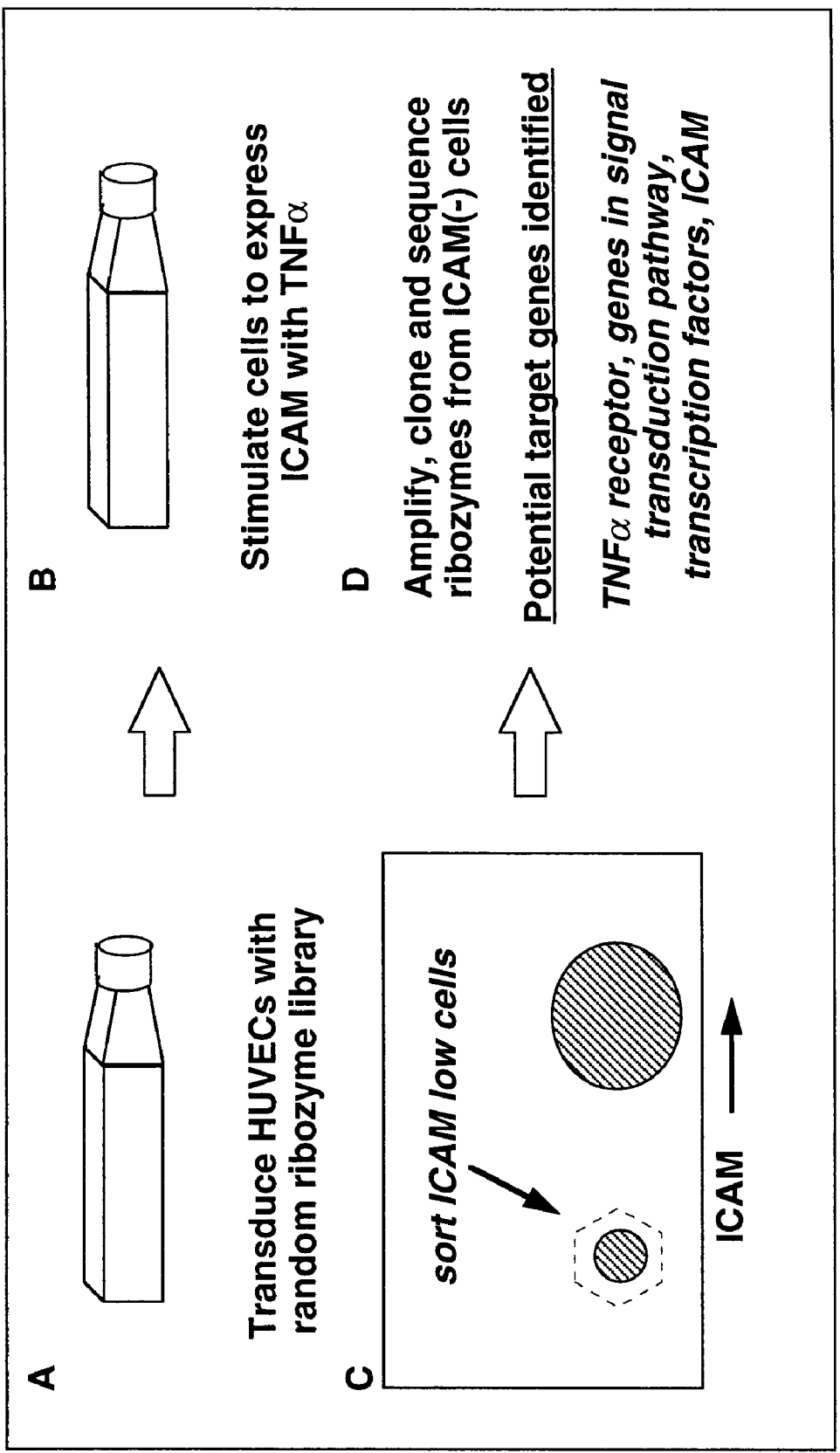

FIG. 11 shows an example of application of Random Ribozyme Libraries to identify genes critical for the induction of ICAM expression. Human Umbilical Vein Endothelial Cells (HUVECs) are transduced with a Random Ribozyme Library (A), ICAM expression is induced using TNF-alpha (13), and cells expressing ribozymes that inhibit ICAM induction are selected from cells expressing ineffective ribozymes by sorting ICAM-low cells (C). Genes critical for ICAM induction are identified by sequencing the binding arms of the ribozymes that inhibit ICAM expression in the ICAM-low cells.

Figure 12:
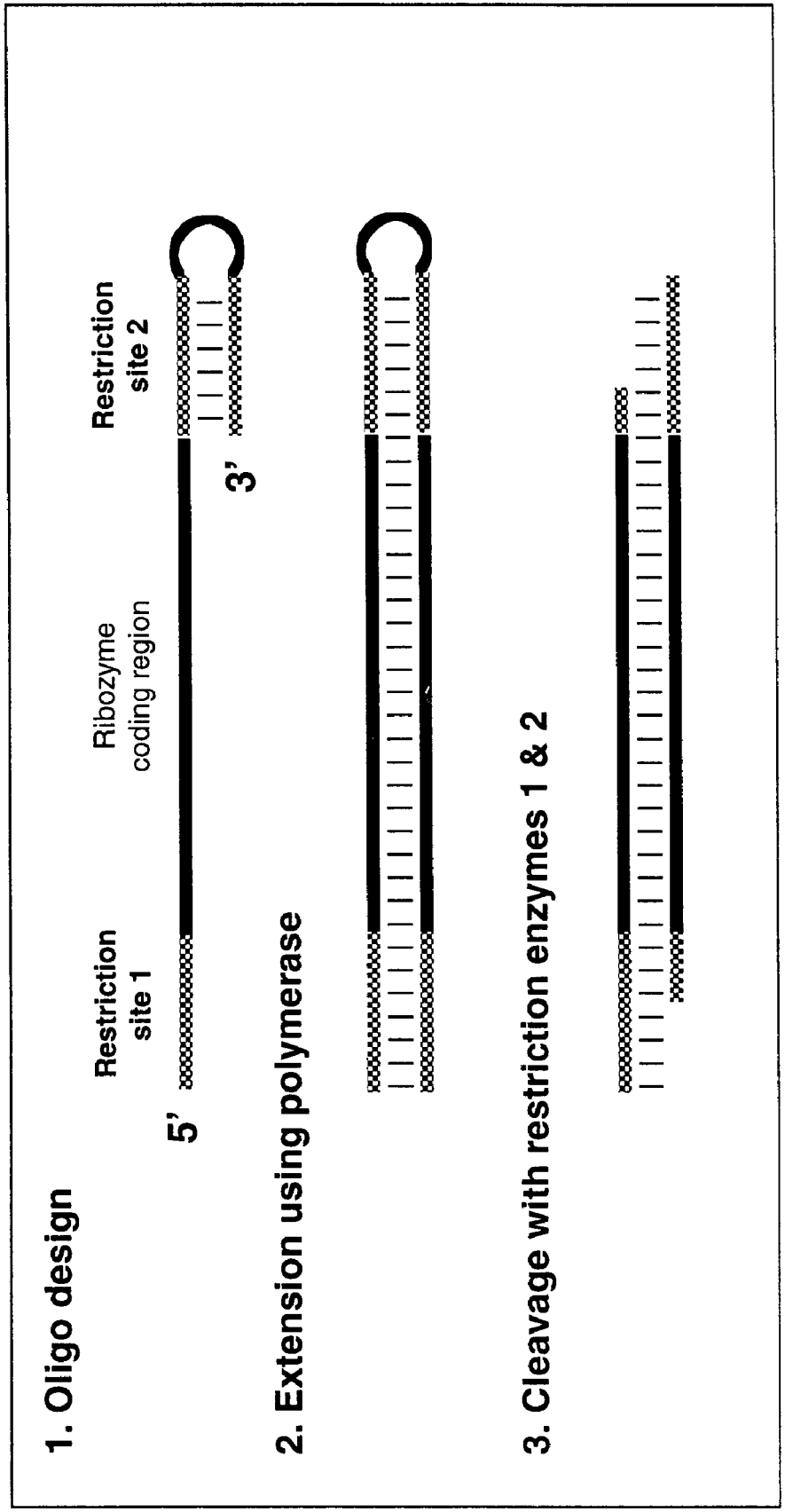

FIG. 12 is an example of an efficient cloning strategy for producing a Defined or Random Ribozyme Libraries. DNA oligos encoding ribozyme coding regions and restriction sites for cloning are designed to also contain a stem-loop structure on the 3' ends (A). This stem loop forms an intramolecular primer site for extension to form a double-stranded molecule by DNA polymerase (B). The double-stranded fragment is cleaved with appropriate restriction endonucleases to produce suitable ends for subsequent cloning (C).

Figure 13:
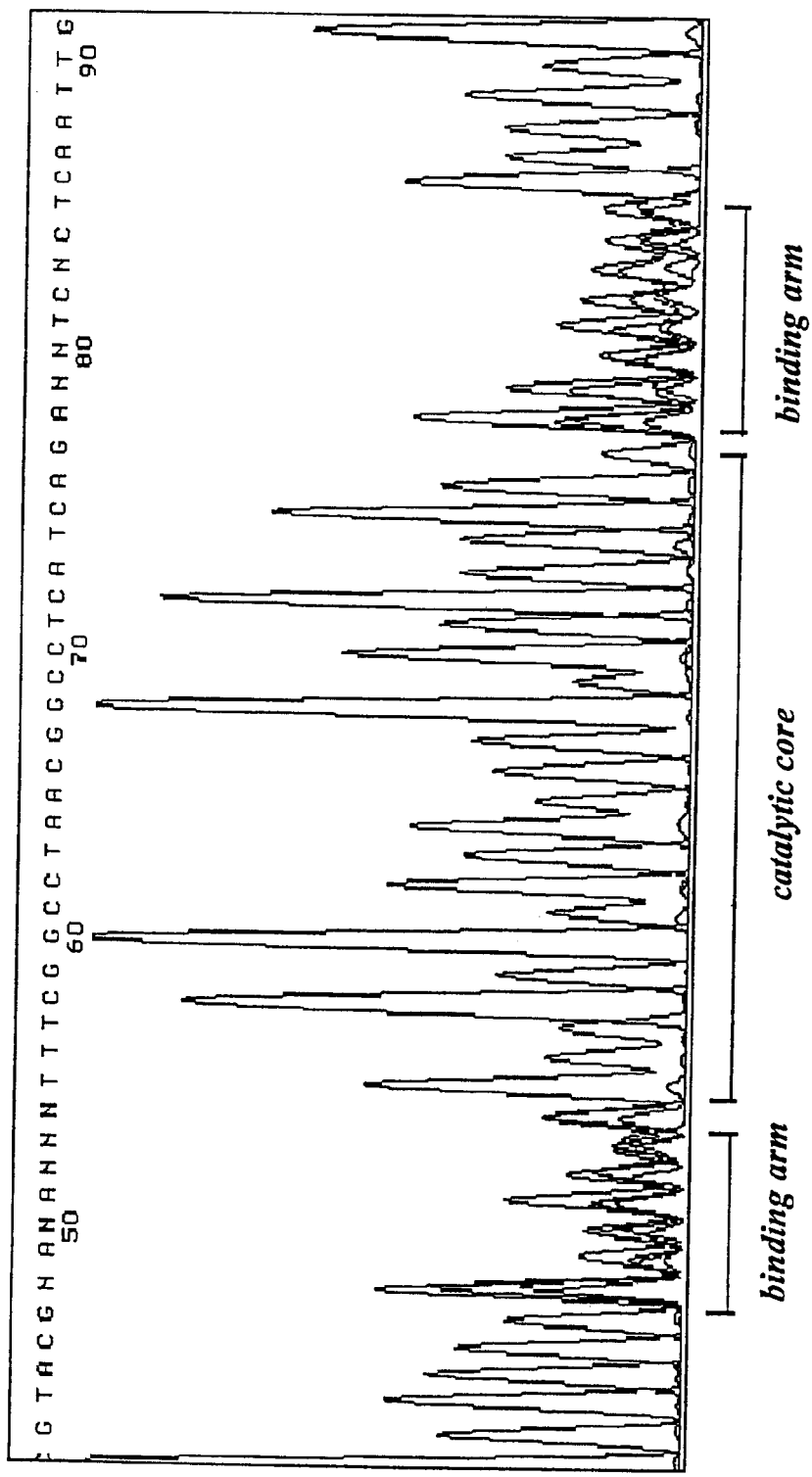

FIG. 13 shows molecular analysis of the PNP-targeted Defined Ribozyme Library: sequence analysis. Plasmid DNA from the targeted Defined Ribozyme Library was prepared and sequenced as a pool. The sequencing primer used reads the non-coding strand of the region encoding the ribozymes. Note that the sequence diverges at the binding arm, converges at the catalytic domain (5'-TTTCGGCCTAACGGCCTCATCAG-3' (SEQ ID NO. 1)), and then diverges at the other binding arm. These results are consistent with those expected for a sequence of a heterogenerous pool of clones containing different sequences at the ribozyme binding arm.

Figure 14:
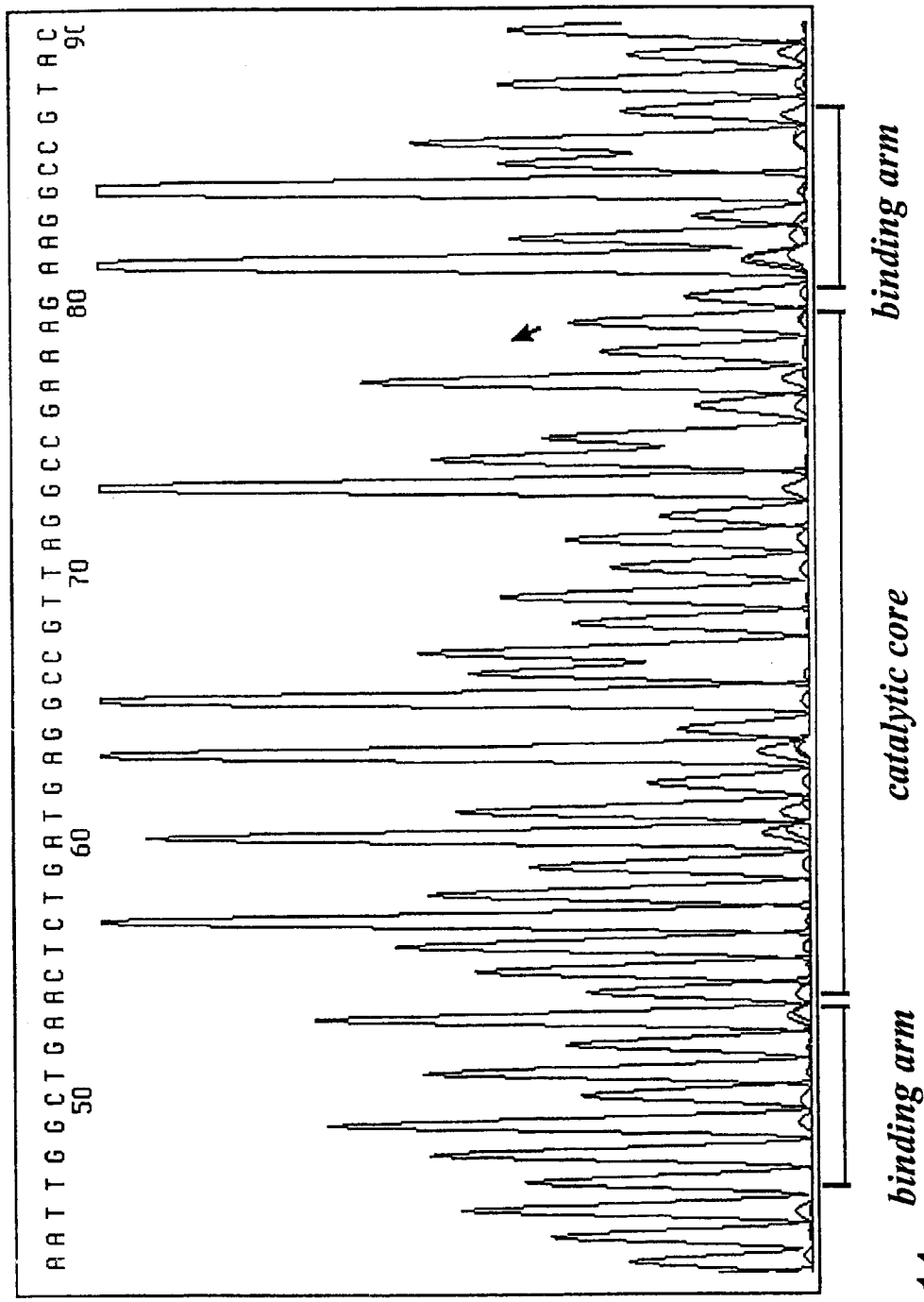
Figure 15A:
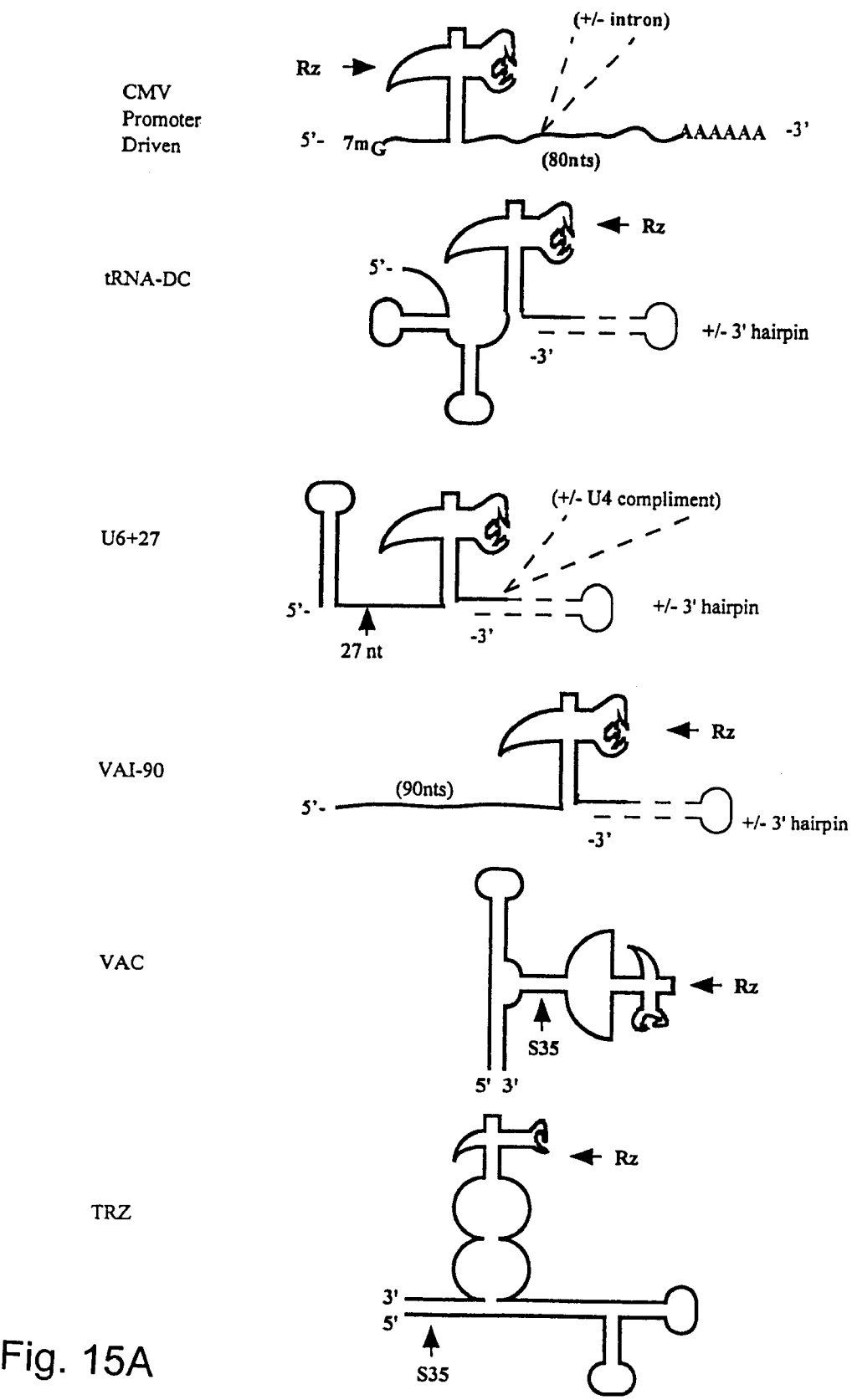
Figure 15B:
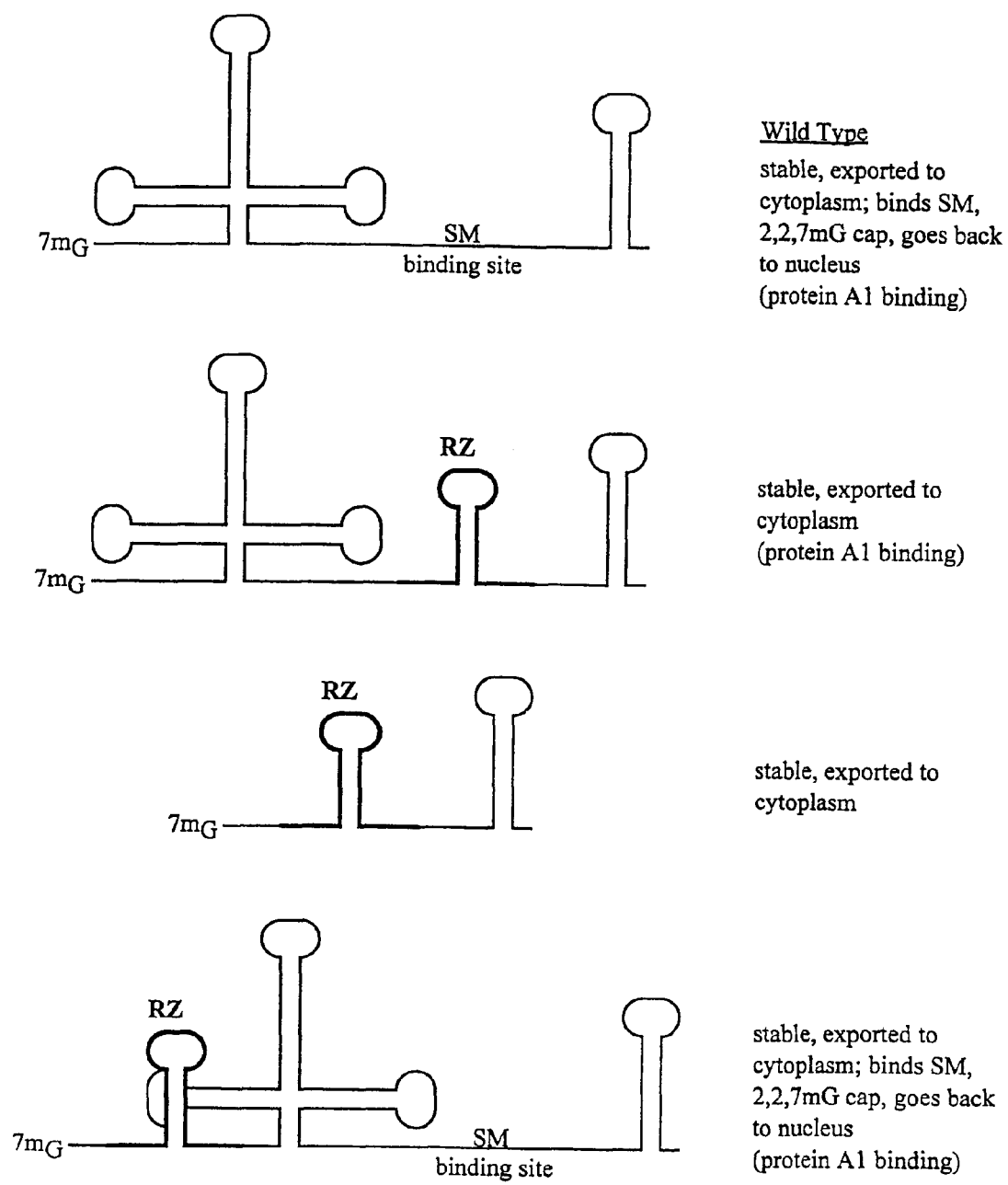
Figure 15C:
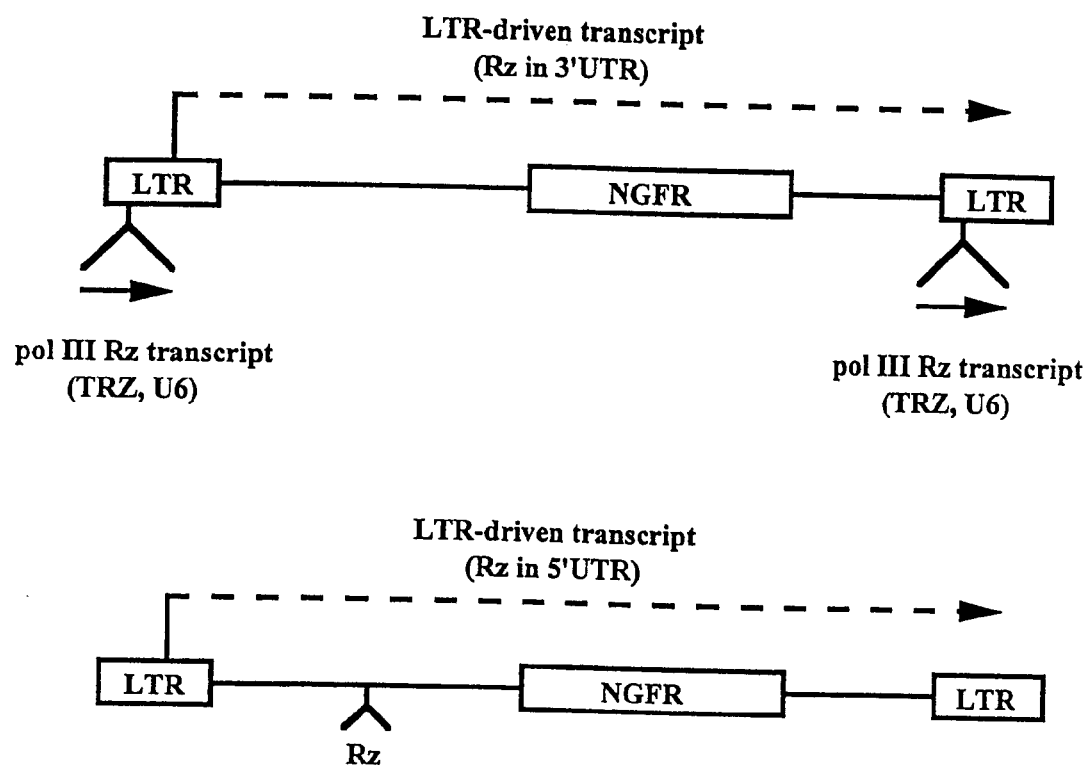

FIG. 14 shows molecular analysis of the PNP-targeted Defined Ribozyme Library: sequence analysis after propagation in Sup T1 human T cells and selection in 10 mmol 6-thioguanosine. Sup T1 cells were transduced with retroviral vector-based Defined Ribozyme Library comprised of 40 different PNP-targeted ribozyme oligos cloned into the U6+27 transcription unit (FIG. 15D). The cells were propagated for 2 weeks following transduction, then subjected to 16 days of selection in 10 mmol 6-thioguanosine. Surviving cells were harvested, and ribozyme sequences present in the selected population were amplified and sequenced. Note that, relative to the original Library where sequences of the binding arms were ambiguous due to the presence of 40 different ribozymes (FIG. 13), the sequence of the binding arms in the selected population corresponded to only 1 of the 40 ribozymes included in the Library. These results suggest that this ribozyme was the most-potent ribozyme of 40 ribozymes tested.

FIGS. 15A–D are a schematic representation of transcription units suitable for expression ribozyme library of the instant invention. 15A is a diagrammatic representation of some RNA polymerase (Pol) II and III ribozyme (RZ) transcription units. CMV Promoter Driven is a Pol II transcript driven by a cytomegalovirus promoter; the transcript can designed such that the ribozyme is at the 5'- region, 3'-region or some where in between and the transcript optionally comprises an intron. tRNA-DC is a Pol III transcript driven by a transfer RNA (tRNA) promoter, wherein the ribozyme is at the 3'-end of the transcript; the transcript optionally comprises a stem-loop structure 3' of the ribozyme. U6+27 is a Pol III transcript driven by a U6 small nuclear (snRNA) promoter; ribozyme is 3' of a sequence that is homologous to 27 nucleotides at the 5'-end of a U6 snRNA; the transcript optionally comprise a stem-loop structure at the 3'-end of the ribozyme. VAI-90 is a Pol III transcript driven by an adenovirus VA promoter; ribozyme is 3' of a sequence homologous to 90 nucleotides at the 5'-end of a VAI RNA; the transcript optionally comprises a stem-loop structure at the 3'-end of the ribozyme. VAC is a Pol III transcript driven by an adenovirus VAI promoter; the ribozyme is inserted towards the 3'-region of the VA RNA and into a S35 motif, which is a stable greater than or equal to 8 bp long intramolecular stem formed by base-paired interaction between sequences in the 5'-region and the 3'-region flanking the ribozyme (see Beigelman et al., International PCT Application No. WO 96/18736); the S35 domain positions the ribozyme away from the main transcript as an independent domain. TRZ is a Pol III transcript driven by a tRNA promoter; ribozyme is inserted in the S35 domain and is positioned away from the main transcript (see Beigelman et al., International PCT Application No. WO 96/18736). 15B shows various transcription units based on the U1 small nuclear RNA (snRNA) system. 15C is a schematic representation of a retroviral vectors encoding ribozyme genes. NGFR, nerve growth factor receptor is used as a selectable marker, LTR, long terminal repeat of a retrovirus, UTR, untranslated region. 15D shows a U6+27 hammerhead ribozyme transcription unit based on the U6 snRNA. The ribozyme transcript comprises the first 27 nt from the U6 snRNA which is. reported to be necessary for the stability of the transcript. The transcript terminates with a stretch of uridine residues. The hammerhead ribozyme shown in the figure has random (N) binding arm sequence.

FIG. 16. Is a diagram illustrating the steps involved in the discovery of genes related to male sterility using Random Library. Following the synthesis of a library of ribozyme oligonucleotides, a clone of the library is generated which is transfected into plant cells with agrobacterium technology (U.S. Pat. No. 5,177,010 to University of Toledo, U.S. Pat. No. 5,104,310 to Texas A&M, European Pat. Application 0131624B1, European Patent Applications 120516, 159418B1 and 176,112 to Schilperoot, U.S. Pat. Nos. 5,149, 645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus). The plant cells are developed into whole plants and those which exhibit male sterility are analyzed to determine the gene sequence.

FIG. 17 is a diagrammatic representation of multimer and monomer random library constructs. N represents independently a nucleotide which may be same or different, HH represents a hammerhead motif, and HP represents a hairpin motif. FIG. 17.A is a schematic representation of a nucleic acid catalyst with a hammerhead motif which is transcribed from a monomer random library construct. FIG. 17.B is a schematic representation of a nucleic acid catalyst with a hairpin motif which is transcribed from a monomer random library construct. FIG. 17.C is a schematic representation of a multimer random library construct comprised of hammerhead motifs. FIG. 17.D is a schematic representation of a multimer random library construct comprised of a mixture of hairpin and hammerhead motifs. Screening Methods:

Applicant has developed an efficient and rapid method for screening libraries of catalytic nucleic acid molecules capable of performing a desired function in a cell. The invention also features the use of a catalytic nucleic acid library to modulate certain attributes or processes in a biological system, such as a mammalian cell, and to identify and isolate a) nucleic acid catalysts from the library involved in modulating the cellular process/attribute of interest; and b) modulators of the desired cellular process/attribute using the sequence of the nucleic acid catalyst.

More specifically, the method of the instant invention involves designing and constructing a catalytic nucleic acid library, where the catalytic nucleic acid includes a catalytic and a substrate binding domain, and the substrate binding domain (arms) are randomized. This library of catalytic nucleic acid molecules with randomized binding arm(s) are used to modulate certain processes/attributes in a biological system. The method described in this application involves simultaneous screening of a library or pool of catalytic nucleic acid molecules with various substitutions at one or more positions and selecting for ribozymes with desired function or characteristics or attributes. This invention also features a method for constructing and selecting for catalytic nucleic acid molecules for their ability to cleave a given target nucleic acid molecule or an unknown target nucleic acid molecule (e.g., RNA), and to inhibit the biological function of that target molecule or any protein encoded by it.

It is not necessary to know either the sequence or the structure of the target nucleic acid molecule in order to select for catalytic nucleic acid molecules capable of cleaving the target in this cellular system. The cell-based screening protocol described in the instant invention (ie., one which takes place inside a cell) offers many advantages over extracellular systems, because the synthesis of large quantities of RNA by enzymatic or chemical methods prior to assessing the efficacy of the catalytic nucleic acid molecules is not necessary. The invention further describes a rapid method of using catalytic nucleic acid molecule libraries to identify the biological function of a gene sequence inside a cell. Applicant describes a method of using catalytic nucleic acid molecule libraries to identify a nucleic acid molecule, such as a gene, involved in a biological process; this nucleic acid molecule may be a known molecule with a known function, or a known molecule with a previously undefined function or an entirely novel molecule. This is a rapid means for identifying, for example, genes involved in a cellular pathway, such as cell proliferation, cell migration, cell death, and others. This method of gene discovery is not only a novel approach to studying a desired biological process but also a means to identify active reagents that can modulate this cellular process in a precise manner.

Applicant describes herein, a general approach for simultaneously assaying the ability of one or more members of a catalytic nucleic acid molecule library to modulate certain attributes/process(es) in a biological system, such as plants, animals or bacteria, involving introduction of the library into a desired cell and assaying for changes in a specific "attribute", "characteristic" or "process". The specific attributes may include cell proliferation, cell survival, cell death, cell migration, angiogenesis, tumor volume, tumor metastasis, levels of a specific mRNA(s) in a cell, levels of a specific protein(s) in a cell, levels of a specific protein secreted, cell surface markers, cell morphology, cell differentiation pattern, cartilage degradation, transplantation, restenosis, viral replication, viral load, and the like. By modulating a specific biological pathway using a catalytic nucleic acid molecule library, it is possible to identify the gene(s) involved in that pathway, which may lead to the discovery of novel genes, or genes with novel function. This method provides a powerful tool to study gene function inside a cell. This approach also offers the potential for designing novel catalytic oligonucleotides, identifying ribozyme accessible sites within a target, and for identifying new nucleic acid targets for ribozyme-mediated modulation of gene expression.

In another aspect the invention involves synthesizing a Random Binding Arm Nucleic Acid Catalyst Library (Random Library) and simultaneously testing all members of the Random Library in cells. This library has ribozymes with random substrate binding arm(s) and a defined catalytic domain. Cells with an altered attribute (such as inhibition of cell proliferation) as a result of interaction with the members of the Random Library are selected and the sequences of the ribozymes from these cells are determined. Sequence information from the binding arm(s) of these ribozymes can be used to isolate nucleic acid molecules that are likely to be involved in the pathway responsible for the desired cellular attribute using standard technology known in the art, e.g., nucleic acid amplification using techniques such as polymerase chain reaction (PCR). This method is a powerful means to isolate new genes or genes with new function.

By "Random Library" as used herein is meant ribozyme libraries comprising all possible variants in the binding arm (s) of a given ribozyme motif Here the complexity and the content of the library is not defined. The Random Library is expected to comprise sequences complementary to every potential target sequence, for the ribozyme motif chosen, in the genome of an organism. The Random Library can be a monomer or a multimer Random Library (see FIG. 17). By monomer Random Library is meant that one ribozyme unit with random binding arms. By multimer Random Library is meant that a transcription unit includes more than one ribozyme unit. The number of ribozyme units are preferably 2, 3,4, 5, 6,7, 8,9, or 10. More specifically, the multimer is comprised of at least one hammerhead molecule, hairpin molecule, hepatitis delta virus (HDV) (FIG. 4), group I intron, RNaseP RNA (in association with an RNA guide sequence) or Neurospora VS RNA. This Random Library can be used to screen for ribozyme cleavage sites in a known target sequence or in a unknown target. In the first instance, the Random Library is introduced into the cell of choice and the expression of the known target gene is assayed. Cells with an altered expression of the target will yield the most effective ribozyme against the known target. In the second instance, the Random Library is introduced into the cell of choice and the cells are assayed for a specific attribute, for example, survival of cells. Cells that survive the interaction with the Random Library are isolated and the ribozyme sequence from these cells is determined. The sequence of the binding arm of the ribozyme can then be used as probes to isolate the gene(s) involved in cell death. Because, the ribozyme(s) from the Random Library is able to modulate (e.g., down regulate) the expression of the gene(s) involved in cell death, the cells are able to survive under conditions where they would have otherwise died. This is a novel method of gene discovery. This approach not only provides the information about mediators of certain cellular processes, but also provides a means to modulate the expression of these modulators. This method can be used to identify modulators of any cell process in any organism, including but not limited to mammals, plants and bacteria.

The invention provides a method for producing a class of enzymatic cleaving agents which exhibit a high degree of specificity for the nucleic acid sequence of a desired target. The enzymatic nucleic acid molecule is preferably targeted to a highly conserved sequence region of a target such that specific diagnosis and/or treatment of a disease or condition can be provided with a single enzymatic nucleic acid.

In one preferred embodiment, a method for identifying a nucleic acid molecule involved in a process in a cell is described, including the steps of: a) synthesizing a library of nucleic acid catalysts, having a substrate binding domain and a catalytic domain, where the substrate binding domain has a random sequence; b) testing the library in the cell under conditions suitable to cause the process in the cell to be altered (such as: inhibition of cell proliferation, inhibition of angiogenesis, modulation of growth and/or differentiation, and others); c) isolating and enriching the cell with the altered process; d) identifying and isolating the nucleic acid catalyst in the altered cell; e) using an oligonucleotide, having the sequence homologous to the sequence of the substrate binding domain of the nucleic acid catalyst isolated from the altered cell, as a probe to isolate the nucleic acid molecule from the cell or the altered cell. Those nucleic acid molecules identified using the selection/screening method described above are likely to be involved in the process that was being assayed for alteration by the member(s) of the ribozyme library. These nucleic acid molecules may be new gene sequences, or known gene sequences, with a novel function. One of the advantages of this method is that nucleic acid sequences, such as genes, involved in a biological process, such as differentiation, cell growth, disease processes including cancer, tumor angiogenesis, arthritis, cardiovascular disease, inflammation, restenosis, vascular disease and the like, can be readily identified using the Random Library approach. Thus theoretically, one Random Library for a given ribozyme motif can be used to assay any process in any biological system.

In another preferred embodiment the invention involves synthesizing a Defined Arm Nucleic Acid Catalyst Library (Defined Library) and simultaneously testing it against known targets in a cell. The library includes ribozymes with binding arm(s) of known complexity (Defined) and a defined catalytic domain. Modulation of expression of the target gene by ribozymes in the library will cause the cells to have an altered phenotype. Such cells are isolated and the ribozymes in these cells are the ones most suited for modulating the expression of the desired gene in the cell.

By "Defined Library" as used herein is meant a library of nucleic acid catalysts, wherein each member nucleic acid catalyst is designed and produced independently,. then added to the library. Thus, the content, complexity (number of different ribozymes contained in the library) and ratios of library members are defined at the outset. Defined Library comprises >2 ribozymes. The process involves screening the sequence of the known target RNA for all possible sites that can be cleaved by a given ribozyme motif and as described, for example in McSwiggen, U.S. Pat. No. 5,525,468, incorporated by reference herein. Synthesizing a representative number of different ribozymes against the target sequence. Combining the ribozymes and introducing the pooled ribozymes into a biological system comprising the target RNA under conditions suitable to facilitate modulation of the expression of the target RNA in said biological system.

Thus, in one aspect, the invention features ribozymes that modulate gene expression in a cell. These nucleic acid catalyst molecules contain substrate binding domains that bind to accessible regions of specific target nucleic acid molecules. The nucleic acid molecules also contain domains that catalyze the cleavage of target. Upon binding, the enzymatic nucleic acid molecules cleave the target molecules, preventing for example, translation and protein accumulation. In the absence of the expression of the target gene, cell proliferation, for example, is inhibited.

Figure 1:
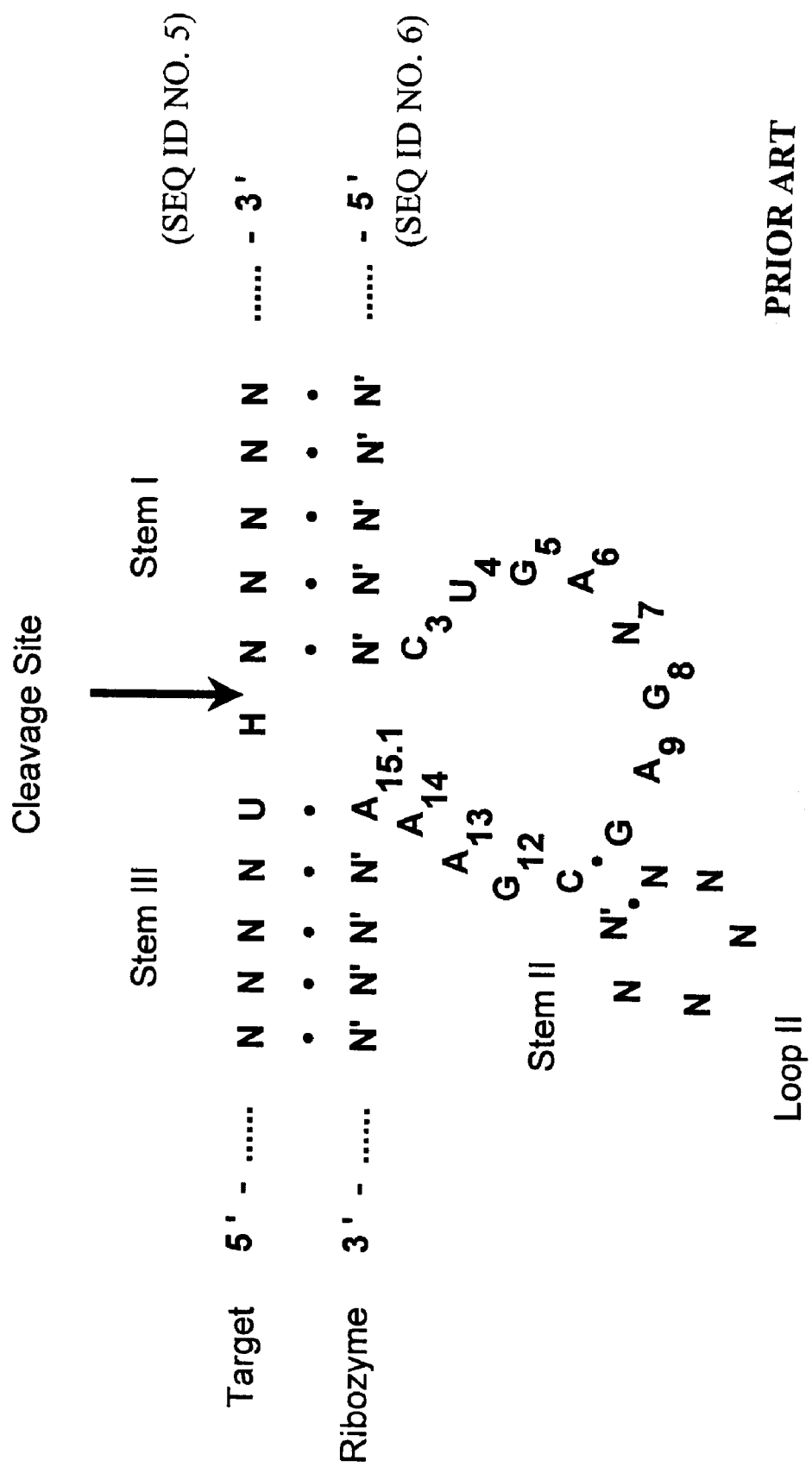

In preferred embodiments, of this invention, the enzymatic nucleic acid molecule is formed in a hammerhead (see for example FIGS. 1–2) or hairpin motif (FIG. 3), but may also be formed in the motif of a hepatitis delta virus (HDV) (FIG. 4), group I intron, RNaseP RNA (in association with an RNA guide sequence) or Neurospora VS RNA FIG. 5). Examples of such hammerhead motifs are described by Rossi et al., 1992, *Aids Research and Human Retrovineses* 8, 183, of hairpin motifs by Hampel et al., EP0360257, Hampel and Tritz, 1989 *Biochemistry* 28, 4929, and Hampel et al., 1990 *Nucleic Acids Res.* 18, 299; Chowrira et al., U.S. Pat. No. 5,631,359, and an example of the hepatitis delta virus motif is described by Perrotta and Been, 1992 *Biochemistry* 31, 16; of the RNaseP motif by Guerrier-Takada et al., 1983 *Cell* 35, 849 and Forster and Altman, 1990 *Science* 249, 783, Neurospora VS RNA ribozyme motif is described by Collins (Saville and Collins, 1990 *Cell* 61, 685–696; Saville and Collins, 1991 *Proc. Natl. Acad. Sci. U.S.A* 88, 8826–8830; Guo and Collins, 1995 *EMBO J.* 14, 368) and of the Group I intron by Zaug et al., 1986, *Nature*, 324, 429; Cech et al., U.S. Pat. No. 4,987,071. These specific motifs are not limiting in the invention and those skilled in the art will recognize that all that is important in an enzymatic nucleic acid molecule with endonuclease activity of this invention is that it has a specific substrate binding site which is complementary to one or more of the target gene RNA and that it have nucleotide sequences within or surrounding that substrate binding site which impart an RNA cleaving activity to the molecule. The length of the binding site varies for different ribozyme motifs, and a person skilled in the art will recognize that to achieve an optimal ribozyme activity the length of the binding arm should be of sufficient length to form a stable interaction with the target nucleic acid sequence.

The enzymatic nucleic acid molecules of the instant invention can be expressed within cells from eukaryotic promoters (e.g., Izant and Weintraub, 1985 *Science* 229, 345; McGarry and Lindquist, 1986 *Proc. Natl. Acad. Sci. U.S.A* 83, 399; Scanlon et al., 1991, *Proc. Natl. Acad. Sci. U.S.A*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 553–4; Ojwang et al, 1992 *Proc. Natl. Acad. Sci. U.S.A* 89, 10802–6; Chen et al., 1992 *Nucleic Acids Res.*, 20, 4581–9; Sarver et al., 1990 *Science* 247, 1222–1225; Thompson et al., 1995 *Nucleic Acids Res.* 23, 2259; Good et al., 1997, *Gene Therapy*, 4, 45; all of the references are hereby incorporated in their totality by reference herein). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO 93/23569, and Sullivan et al., PCT WO 94/02595; Ohkawa et al, 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856; all of the references are hereby incorporated in their totality by reference herein).

By "vectors" is meant any nucleic acid- and/or viral-based technique used to deliver a desired nucleic acid.

In another aspect of the invention, enzymatic nucleic acid molecules that cleave target molecules are expressed from transcription units (see for example FIG. 15) inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target MRNA. The active ribozyme contains an enzymatic center or core equivalent to those in the examples, and binding arms able to bind target nucleic acid molecules such that cleavage at the target site occurs. Other sequences may be present which do not interfere with such cleavage. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review see Couture and Stinchcomb, 1996, *TIG.*, 12, 510).

In a preferred embodiment, an expression vector comprising nucleic acid sequence encoding at least one of the nucleic acid catalyst of the instant invention is disclosed. The nucleic acid sequence encoding the nucleic acid catalyst of the instant invention is operable linked in a manner which allows expression of that nucleic acid molecule.

In one embodiment, the expression vector comprises: a transcription initiation region (e.g., eukaryotic pol I, II or III initiation region); b) a transcription termination region (e.g., eukaryotic pol I, II or III termination region); c) a gene encoding at least one of the nucleic acid catalyst of the instant invention; and wherein said gene is operably linked to said initiation region and said termination region, in a manner which allows expression and/or delivery of said nucleic acid molecule. The vector may optionally include an open reading frame (ORF) for a protein operably linked on the 5' side or the 3'-side of the gene encoding the nucleic acid catalyst of the invention; and/or an intron (intervening sequences).

Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Nail. Acad. Sci. U S A*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. U.S.A*, 89, 10802–6; Chen et al., 1992 *Nucleic Acids Res.*, 20, 4581–9; Yu et al., 1993 *Proc. Natl. Acad. Sci. U.S.A*, 90, 6340–4; L'Huillier et al., 1992 *EMBO J.* 11, 4411–8; Lisziewicz et al., 1993 *Proc. Natl. Acad. Sci. U S. A.*, 90, 8000–4; Thompson et al., 1995 *Nucleic Acids Res.* 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as ribozymes in cells (Thompson et al, supra; Couture and Stinchcomb, 1996, supra; Noonberg et al., 1994, *Nucleic Acid Res.*, 22, 2830; Noonberg et al., U.S. Pat. No. 5,624,803; Good et al., 1997, *Gene Ther.* 4, 45; Beigelman et al, International PCT Publication No. WO 96/18736; all of these publications are incorporated by reference herein. Examples of transcription units suitable for expression of ribozymes of the instant invention are shown in FIG. 15. The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In a preferred embodiment an expression vector comprising nucleic acid sequence encoding at least one of the catalytic nucleic acid molecule of the invention, in a manner which allows expression of that nucleic acid molecule. The expression vector comprises in one embodiment; a) a transcription initiation region; b) a transcription termination region; c) a gene encoding at least one said nucleic acid molecule; and wherein said gene is operably linked to said initiation region and said termination region, in a manner which allows expression and/or delivery of said nucleic acid molecule. In another preferred embodiment the expression vector comprises: a) a transcription initiation region; b) a transcription termination region; c) an open reading frame; d) a gene encoding at least one said nucleic acid molecule, wherein said gene is operably linked to the 3'-end of said open reading frame; and wherein said gene is operably linked to said initiation region, said open reading frame and said termination region, in a manner which allows expression and/or delivery of said nucleic acid molecule. In yet another embodiment the expression vector comprises: a) a transcription initiation region; b) a transcription termination region; c) an intron; d) a gene encoding at least one said nucleic acid molecule; and wherein said gene is operably linked to said initiation region, said intron and said termination region, in a manner which allows expression and/or delivery of said nucleic acid molecule. In another embodiment, the expression vector comprises: a) a transcription initiation region; b) a transcription termination region; c) an intron; d) an open reading frame; e) a gene encoding at least one said nucleic acid molecule, wherein said gene is operably lined to the 3'-end of said open reading frame; and wherein said gene is operably linked to said initiation region, said intron, said open reading frame and said termination region, in a manner which allows expression and/or delivery of said nucleic acid molecule.

In a preferred embodiment, the invention features a method of synthesis of enzymatic nucleic acid molecules of instant invention which follows the procedure for normal chemical synthesis of RNA as described in Usman et al., 1987 *J. Am. Chem. Soc.*, 109, 7845; Scaringe et al., 1990 *Nucleic Acids RES.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 $\mu$mol scale protocol with a 5 min coupling step for alklsilyl protected nucleotides and 2.5 min coupling step for 2'-O-methylated nucleotides. Table II outlines the amounts, and the contact times, of the reagents used in the synthesis cycle. A 6.5-fold excess (163 $\mu$L of 0.1 M=16.3 $\mu$mol) of phosphoramidite and a 24-fold excess of S-ethyl tetrazole (238 $\mu$L of 0.25 M=59.5 $\mu$mol) relative to polymer-bound 5'-hydroxyl is used in each coupling cycle. Average coupling yields on the 394 Applied Biosystems, Inc. synthesizer, determined by calorimetric quantitation of the trityl fractions, is 97.5–99%. Other oligonucleotide synthesis reagents for the 394 Applied Biosystems, Inc. synthesizer: detritylation solution was 2% TCA in methylene chloride (ABI); capping was performed with 16% N-methyl, imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile is used directly from the reagent bottle. S-Ethyl tetrazole solution (0.25 M in acetonitrile) is made up from the solid obtained from American International Chemical, Inc.

In a preferred embodiment, deprotection of the chemically synthesized nucleic acid catalysts of the invention is performed as follows. The polymer-bound oligoribonucleotide, trityl-off, is transferred from the synthesis column to a 4mL glass screw top vial and suspended in a solution of methylamine MA) at 65° C. for 10 min. After cooling to −20° C., the supernatant is removed from the polymer support. The support is washed three times with 1.0 mL of EtOH:MeCN:$H_2O$/3:1:1, vortexed and the supernatant is then added to the first supernatant. The combined supernatants, containing the oligoribonucleotide, are dried to a white powder.

The base-deprotected oligoribonucleotide is resuspended in anhydrous TEA.HF/NMP solution (250 $\mu$L of a solution of 1.5 mL N-methylpyrrolidinone, 750 $\mu$L TEA and 1.0 mL TEA.3HF to provide a 1.4M HF concentration) and heated to 65° C. for 1.5 h. The resulting, fully deprotected, oligomer is quenched with 50 mM TEAB (9 mL) prior to anion exchange desalting.

For anion exchange desalting of the deprotected oligomer, the TEAB solution is loaded on to a Qiagen 500® anion exchange cartridge (Qiagen Inc.) that is pre-washed with 50 mM TEAB (10 mL). After washing the loaded cartridge with 50 mM TEAB (10 mL), the RNA is eluted with 2 M TEAB (10 mL) and dried down to a white powder. The average stepwise coupling yields are generally >98% (Wincott et al., 1995 *Nucleic Acids Res.* 23, 2677–2684).

Ribozymes of the instant invention are also synthesized from DNA templates using bacteriophage T7 RNA polymerase (Milligan and Uhlenbeck, 1989, *Methods Enzymol.* 180, 51).

Ribozymes are purified by gel electrophoresis using general methods or are purified by high pressure liquid chromatography (HPLC; See Wincott et al., supra) the totality of which is hereby incorporated herein by reference) and are resuspended in water.

By "nucleotide" as used herein is as recognized in the art to include natural bases (standard), and modified bases well known in the art. Such bases are generally located at the 1' position of a sugar moiety. Nucleotide generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al, 1996, *Biochemistry*, 35, 14090). By "modified bases" in this aspect is meant nucleotide bases other than adenine, guanine, cytosine and uracil at 1' position or their equivalents; such bases may be used within the catalytic core of the enzyme and/or in the substrate-binding-regions.

In another preferred embodiment, catalytic activity of the molecules described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 Trends in Biochem. Sci. 17, 334; Usman et al, International Publication No. WO 93/15187; and Rossi et al., International Publication No. WO 91/03162; Sproat, U.S. Pat. No. 5,334, 711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein).

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modification of enzymatic nucleic acid molecules have been extensively described in the art (see Eckstein et al., *International Publication* PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. *International Publication* PCT No. WO 93/15187; Sproat, U.S. Pat. No. 5,334,711 and Beigehnan et al., 1995 *J. Biol. Chem.* 270, 25702; all of the references are hereby incorporated in their totality by reference herein).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (3urgin et al, 1996, *Biochemistry*, 35, 14090). Such ribozymes herein are said to "maintain" the enzymatic activity on all RNA ribozyme.

In a preferred embodiment, the enzymatic nucleic acid molecules of the invention are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. Using the methods described herein, other enzymatic nucleic acid molecules that cleave target nucleic acid may be derived and used as described above. Specific examples of nucleic acid catalysts of the instant invention are provided below in the Tables and figures.

Sullivan, et al., WO 94/02595, describes the general methods for delivery of enzymatic nucleic acid molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable—nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., WO 93/23569 which have been incorporated by reference herein.

Such enzymatic nucleic acid molecules can be delivered exogenously to specific cells as required. In the preferred hammerhead motif the small size (less than 60 nucleotides, preferably between 30–40 nucleotides in length) of the molecule allows the cost of treatment to be reduced.

Therapeutic ribozymes delivered exogenously must remain stable within cells until translation of the target RNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes by introducing nucleotide modifications to enhance their nuclease stability as described above.

EXAMPLES

The following are non-limiting examples showing the synthesis, screening and testing of catalytic nucleic acids of the instant invention.

Example 1

Oligonucleotide Design and Preparation for Cloning Defined and Random Libraries

The DNA oligonucleotides used in this study to construct Defined and Random Ribozyme Libraries were purchased from Life Technologies (BRL). A schematic of the oligonucleotide design used to construct said Defined or Comprehensive Ribozyme Libraries is shown in FIG. 12. This example is meant to illustrate one possible means to construct such libraries. The methods described herein are not meant to be inclusive of all possible methods for constructing such libraries. The oligonucleotides used to construct the hammerhead ribozyme libraries were designed as follows:

5'-CGAAATCAATTG-(N1) (SEQ ID NO.2)-{CatalyticCore}-(N2)$_x$-CGTACGACACGAAAGTATCG-3'(SEQ ID NO.3)

Where N1=the Stem I target-specific binding arm of length x, Catalytic Core=the hammerhead catalytic domain 5'-CTGATGAGGCCGUUAGGCCGAAA-3' (SEQ ID NO. 4), and N2=the Stem III target specific binding arm of length x. The oligonucleotides were designed to self-prime via formation of a stem-loop structure encoded at the 3' ends of the oligos (FIG. 12A). This intramolecular interaction favored an unbiased extension of complex pools of ribozyme-encoding oligonucleotides. In the case of Defined Ribozyme Library described below (FIGS. 13–14), N1 and N2 were 8 nt each and were designed to be complimentary to the RNA encoded by the purine nucleoside phosphorylase (PNP) gene. In the case of Random Ribozyme Libraries, N1 and N2 were randomized during synthesis to produce a single pool of all possible hammerhead ribozymes.

In the example shown (FIGS. 13–14), oligonucleotides encoding 40 different PNP-specific hammerhead ribozymes (greater than 40 ribozymes can be used) were pooled to a final concentration of 1 µM total oligonucleotides (2.5 nM each individual oligo). Oligos were heated to 68° C. for 30 min and then cooled to ambient temperature to promote formation of the 3'. stem-loop for self-priming (FIG. 12A). The 3' stem loop was extended (FIG. 12B) using Klenow DNA polymerase (1 µM total oligonucleotides in 1 ml of 50 mM Tris pH 7.5, 10 mM MgCl2, 100 µg/ml BSA. 25 µg M dNTP mix, and 200 U Klenow) by incubating for 30 min at 37° C. The reaction mixtures were then heated to 65° C. for 15 min to inactivate the polymerase. The double-stranded oligos (approximately 30 µg) were digested with the 100 U of the 5' restriction endonuclease Mfe I (NEB) as described by the manufacturer, then similarly digested with the 3' restriction endonuclease BsiWI (FIG. 12C). To reduce the incidence of multiple ribozyme inserts during the cloning steps, the cleaved products were treated with Calf Intestinal Phosphatase (CIP, Boehringer Mannheim) as described by the manufacturer to remove the phosphate groups at the 5' ends. This step inhibits intra- and intermolecular ligation of the ribozyme-encoding fragments. Full-length product corresponding to the double-stranded, restriction digested and phosphatase-treated products was gel-purified following electrophoresis through 10% non-denaturing acrylamide gels prior to cloning to enrich for fill-length material.

Example 2

Cloning of Defined and Random Libraries

The cloning vectors used contained the following cloning sites: 5'-MfeI-Cla I-BsiWI-3'. Vectors were digested with Mfe I and BsiWI prior to use. Thus, vectors cleaved with both enzymes should lack the Cla I site present between the sites, while vectors cleaved with only one of the enzymes should still retain the Cla I site. Pooled oligos were ligated to vector using a 2:1 or 5:1 molar ratio of double-stranded oligo to vector in 50-mL reactions containing 500 ng vector and 5 U ligase in 1×ligase buffer (Boehringer Mannheim). Ligation reactions were incubated over night at 16° C., then heated to 65° C. 10 min to inactivate the ligase enzyme. The desired products contain a single ribozyme insert and lack the original Cla I site included between the Mfe I and BsiWI cloning sites. Any unwanted, background vector lacking ribozyme inserts and thus still containing the Cla I sites were inactivated by cleaving the product with 5 U of the restriction endonuclease Cla I for 1 h at 37° C. Approximately 150 ng of ligated vector was used to transform 100 µl XL-2 Blue competent bacteria as described by the supplier (Stratagene).

Example 3

Simultaneous Screening of 40 Different Ribozymes Targeting PNP Using Defined Ribozyme Libraries A Defined Ribozyme Library containing 40 different hammerhead ribozymes targeting PNP was constructed as described above (FIGS. 12–14). PNP is an enzyme that plays a critical role in the purine metabolic/salvage pathways. PNP was chosen as a target because cells with reduced PNP activity can be readily selected from cells with wild-type activity levels using the drug 6-thioguanosine. This agent is not toxic to cells until it is converted to 6-thioguanine by PNP. Thus, cells with reduced PNP activity are more resistant to this drug and can be selectively grown in concentrations of 6-thioguanosine that are toxic to cells with wild-type activity levels.

The PNP-targeted Defined Ribozyme Library expression vectors were converted into retroviral vector particles, and the resulting particles were used to transduce the Sup T1 human T cell line. A T-cell line was chosen for study because T lymphocytes are more dependent on the purine salvage pathway and thus are highly susceptible to 6-thioguanosine killing. Two weeks after transduction, the cells were. challenged with 10 mmol 6-thioguanosine. Resistant cells began to emerge two weeks after initiation of selection. 6-Thioguanosine-resistant cells were harvested, and the ribozyme-encoding region of the expression vector was amplified using PCR and sequenced. The sequence pattern of the ribozyme region in the selected cells was significantly different from that produced from the starting library shown in FIG. 13. In the original library, sequences of the binding arms were ambiguous due to the presence of all 40 PNP-targeted ribozymes (FIG. 13). However, the sequence of the ribozyme-encoding regions from the 6-thioguanosine selected cells was clearly weighted towards one of the ribozymes contained in the original pool—the ribozyme designed to cleave at nucleotide #32 of PNP mRNA. These data suggests that the ribozyme targeting position 32 of the PNP mRNA appears to be more active than the other 39 PNP-targeted ribozymes included in the pool.

Example 4

Discovery of Genes Involved in Plant Male Sterility

When two genetically distinct plant lines are crossed with each other, a variety of beneficial attributes may be combined into one single hybrid. The use of this technique for the development of hybrid seeds allows for increased agronomic benefits. Desirable attributes for plants include fruit size, growth rate, germination, yield sizes, and disease, temperature, and insect resistance. Generally speaking, this process involves generation of inbred crop lines, breeding between these lines, followed by determination whether the hybrids are superior to the original lines. For this process to be successful however, a means of preventing self-pollination must be implemented to improve cross-pollination rates. Seed generated through self-pollination would contaminate the supply of hybrid seed. By causing male or female sterility in crops, the plants would have to rely on cross breeding to reproduce. Within the context of this application, "male sterility" is defined as a condition in which a plant has functional female reproductive organs but is incapable of self-fertilization. Fertilization of the embryo sac will occur only when the pollen of a second flower comes into contact with the female organs. Alternatively "female sterility" is defined as a condition in which a plant cannot produce viable seeds because of abnormal functioning of the female gametophyte, female gamete, female zygote, or the seed.

Some plants such as corn have spatially separated male and female organs, and therefore removal of the fertile pollen from the plant is sufficient to prevent self-pollination. While functional in corn, this strategy cannot be transferred to other major crop plants since the male and female organs are present within the same flower. Therefore removal of the fertile pollen becomes cumbersome and in may cases economically infeasible. Several strategies for preventing self pollination have been suggested which include chemical and genetic sterilization.

Chemical sterilization involves the use of compounds known as gametocides which can temporarily cause male sterility. The compounds function by killing or blocking pollen production within the flower. The cost of these compounds can be limiting especially since the gametocide must be applied with every occurrence of flower production. Any new flowers which develop following the initial spraying must also be sprayed to prevent cross pollination. The timing of gametocide spraying must be carefully implemented to coincide with flower production which can be problematic because of the difficulty in anticipating the appearance of flowers.

Another mechanism is called cytoplasmic male sterility (CMS) in which a defective mitochondrion causes an inhibition or obstruction of pollen production. Alternatively, the prevention of pollen production can involve alterations within the cell's nucleus. There are a variety of strategies for modulating gene expression in plants. Traditionally, antisense RNA (reviewed in Bourque, 1995 *Plant Sci* 105, 125–149) and co-suppression (reviewed in Jorgensen, 1995 *Science* 268, 686–691) approaches have been used to modulate gene expression. Insertion mutagenesis of genes have also been used to inhibit gene expression. This approach is generally random and does not allow for targeted inhibition of specific genes. Regulation of male sterility through modulation of certain genes responsible for said sterility have also been described. Fabijanski et al. International PCT publication WO 90/08828, describes the use of antisense molecules to downregulate DNA sequences already known in the art to be involved in male sterility. The use of ribozymes for the inhibition of Ms5 locus or Jagl8 derived from *Arabidopsis thaliana* is described in Glover et al., International PCT Publication WO 97/30581. The present invention describes a process for identification of genes involved in male and/or female sterility. Applicant believes that Nucleic Acid Catalyst technology offers an attractive new means to alter gene expression in plants and to discover new genes involved in male nad/or female sterility.

Thus in one aspect of the invention, applicant describes a method for the identification of genes involved in male or female sterility. The Random Library approach is used to discover genes whose down-regulation results in a male sterile phenotype. These genes will likely be involved in microspore, tapetum, filament, pollen and anther formation, as well as anther dehiscence. Examples of known genes involved in male sterile phenotype include Jag18 (WO 97/30581) and gene whose peptide sequence is given in U.S. Pat. No. 5,478,369. Genes have been found by transposon tagging and antisense inhibition, but both methods have drawbacks. Transposon tagging will identify genes that are present as a single copy and where complete inhibition of gene expression will not prohibit plant development. Antisense or cosuppression methods require sequence information, which may be derived from differential expression libraries or random sequencing. Expressed sequence tags are often used as a source of sequence information, but this approach often times ignores or misses low abundance transcripts, like transcription factors, which are often key regulatory elements. The method described herein requires no initial sequence information but allows for sequence information to be obtained in plants demonstrating the desired phenotype.

One non-limiting method for the identification of male sterility gene(s) is illustrated in FIG. 16. A Random Library is constructed from oligonucleotides containing randomized arm sequences surrounding a catalytic core (e.g. Hammerhead motif). The expected frequency of seeing a desired phenotype is related to the. arm length of the ribozyme library (Random Library) and the number of genes involved in the phenotype. For a ribozyme library, for example a hammerhead ribozyme with two binding arms, having seven nucleotides on each arm of the ribozyme (7/7 arm length with random nucleotides), this represents 67 million ribozymes. A Multimer Random Library of ribozymes with an average of 10 ribozyme units covalently attached to each other (approximately 360 nucleotides long) is synthesized to reduce the number of clones that have to be transfected. The Random library of Nucleic Acid Catalyst is transcribed and cloned into expression vectors using methods described above under examples 1 and 2 respectively. The plasmid may also include a gene which confers resistance to a cytotoxic substance (e.g. chlorosulfuron, hygromyacin, PAT and/or bar, bromoxynil, kanamycin and the like), which allows for selection following transfection. These clones are then used to transform agrobacterium using techniques familiar to those skilled in the art (U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus; all are incorporated by reference herein). The recombinant agrobacterium is then used to transform a single plant cell which is capable of regenerating into a whole plant. Other transfection technologies may also be utilized to deliver DNA plasmids into the plant. cell including but not limited to electroporation, liposomes, cationic lipids, $CaCl_2$ precipitation and the like known in the art. The plants cells are then grown into a whole plant and analyzed to determine if complete or partial male sterility exists. Complete male sterility is defined as the state wherein no pollen is produced and/or released causing an inability of the plant to self-fertilize. Partial male sterility is defined as the state wherein reduced or abnormal pollen production or release results compared to normal wild type plants.

To allow for easier observation of sterility in Arabidopsis plant, a strain expressing Green Florescent Protein (GFP) under the control of a pollen-specific promoter is generated. The Arabidopsis line is then transformed with ribozyme libraries expressed under the control of different promoters. A constitutive promoter (such as the CaMV 35S) is utilized for ribozyme expression while a pollen or anther specific promoter is used for the expression of GFP. The constitutively expressed ribozyme(s) from the Random library is likely to identify genes that are tissue specifically regulated under the control of male fertility. The random library comprised of a tissue specific promoter might be able identify genes which are not directly related to reproduction but whose inhibition may nontheless cause male and/or female sterility (e.g. housekeeping genes such as actin). Any reduction in fluorescence is an indication that the inhibition of a gene is linked to or involved in male sterility.

From the plants demonstrating complete or partial male sterility, RNA is purified and the ribozyme RNA is amplified and cloned by RT-PCR. Alternatively or in addition, the ribozyme gene is directly amplified from the genomic DNA using standard molecular biology techniques known in the art. This ribozyme is recloned and retransformed as described above to ensure (confirm) that the phenotype was change is due to ribozyme activity and not due to any insertional mutagenesis. If the trait is recreated, the sequence of the ribozyme binding arm is used as a tag to find the gene involved in the modification of phenotype. Using bioinformatics, available sequences is searched for homology. If no related sequence is found, cDNA libraries can be screened using the 15 nucleotide binding arm sequence as a probe to isolate the gene from the plant using standard molecular biology techniques known in the art.

In yet another aspect of the invention, hybrid seed plants are produced in which one or more genes involved in male sterility are completely or partially inhibited. These genes are individually or in combination inhibited either using the ribozyme(s) that was responsible for the gene's identification, or using other ribozymes. Alternatively, other technologies known in the art, such as antisense, cosuppression, and the like, can also be used to achieve gene inhibition. The transgenic plant, where one or more of the male sterility genes is inhibited, is mated with a suitable male fertile plant causing the synthesis of hybrid seeds. Applicant has developed a method for not only identifying gene(s) involved in biochemical pathways in plants, but has in the process developed a ribozyme that can then be used to specifically down-regulate that gene in plants.

Diagnostic Uses

Enzymatic nucleic acids of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that fall-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of MnRNA whose protein product is implicated in the development of the phenotype is adequate to establish risk. If probes of comparable specific activity are used for both transcripts, then a qualitative comparison of RNA levels will be. adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention might have many of the same applications for the study of RNA that DNA restriction endonucleases have for the study of DNA (Nathans et al., 1975 Ann. Rev. Biochem. 44:273). For example, the pattern of restriction fragments could be used to establish sequence relationships between two related RNAs, and large RNAs could be specifically cleaved to fragments of a size more useful for study. The ability to engineer sequence specificity of the ribozyme is ideal for cleavage of RNAs of unknown sequence.

Other embodiments are within the following claims.

TABLE 1

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintainance of the active structure.
Over 300 known members of this class. Found as an intervening sequence in Tetrahymena thermophila rRNA, fungal mitochondria, chloroplasts, phage T4, blue-green algae, and others.
Major structural features largely established through phylogenetic comparisons, mutagenesis, and biochemical studies [,[1]].

TABLE 1-continued

Characteristics of naturally occurring ribozymes

Complete kinetic framework established for one ribozyme [2,3,4,5].
Studies of ribozyme folding and substrate docking underway [6,7,8].
Chemical modification investigation of important residues well established [9,10].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [11].
RNAse P RNA (M1 RNA)

Size: ~290 to 400 nucleotides.
RNA portion of a ubiquitous ribonucleoprotein enzyme.
Cleaves tRNA precursors to form mature tRNA [12].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [13,14]
Important phosphate and 2' OH contacts recently identified [15,16]
Group II Introns Size: >1000 nucleotides.
Trans cleavage of target RNAs recently demonstrated [17,18].
Sequence requirements not fully determined.
Reaction mechanism: 2'-OH of an internal adenosine generates cleavage products with 3'-OH and a "lariat" RNA containing a 3'–5' and a 2'-5' branch point.
Only natural ribozyme with demonstrated participation in DNA cleavage [19,20] in addition to RNA cleavage and ligation.
Major structural features largely established through phylogenetic comparisons [21].
Important 2' OH contacts beginning to be identified [22]
Kinetic framwork under development [23]
Neurospora VS RNA Size: ~144 nucleotides.
Trans cleavage of hairpin target RNAs recently demonstrated [24].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.
Hammerhead Ribozyme Size: ~13 to 40 nucleotides.
Requires the target sequence UH immediately 5' of the cleavage site.
Binds a variable number nucleotides on both sides of the cleavage site.
Reaction mechanism: attach by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [25,26]
Minimal ligation activity demonstrated (for engineering through in vitro selection)[27]
Complete kinetic framework established for two or more ribozymes [28].
Chemical modification investigation of important residues well established [29].
Hairpin Ribozyme Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satelite RNAs of the tobacco ringspot virus, arabis mosiac virus and chicory yellow mottle virus) which uses RNA as the infectious agent.
Essential structural features largely defined [30,31,-,33]
Ligation activity (in addition to cleavage activity) makes ribozyme amenable to engineering through in vitro selection [34]
Complete kinetic framework established for one ribozyme [35].
Chemical modification investigation of important residues begun [36,37].
Hepatitis Delta Virus (HDV) Ribozyme Size: ~60 nucleotides.
Trans cleavage of target RNAs demonstrated [38].
Binding sites and structural requirements not fully determined, although no sequences 5' of cleavage site are required. Folded ribozyme contains a pseudoknot structure [39].
Reaction mechanism: attack by 2'-OH 5' to the scissile bond to generate cleavage products with 2',3'-cyclic phosphate and 5'-OH ends.

TABLE 1-continued

Characteristics of naturally occurring ribozymes

Only 2 known members of this class. Found in human HDV.
Circular form of HDV is active and shows increased nuclease stability [40]

[1] Michel, Francois; Westhof, Eric. Slippery substrates. Nat. Structure. Biol. (1994), 1(1), 5–7. Lisacek, Frederique; Diaz, Yolande; Michel, Francois. Automatic identification of group I intron cores in genomic DNA sequences. J. Mol. Biol. (1994), 235(4), 1206–17.
[2] Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
[3] Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
[4] Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
[5] Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
[6] Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
[7] Banerjee, Aloke Raj; Turner, Douglas H.. The time dependence of chemical modification reveals slow steps in the folding of a group I ribozyme. Biochemistry (1995), 34(19), 6504–12.
[8] Zarrinkar, Patrick P.; Williamson, James R.. The P9.1–P9.2 peripheral extension helps guide folding of the Tetrahymena ribozyme. Nucleic Acids Res. (1996), 24(5), 854–8.
[9] Strobel, Scott A.; Cech, Thomas R.. Minor groove recognition of the conserved G.cntdot.U pair at the Tetrahymena ribozyme reaction site. Science (Washington, D.C.) (1995), 267 (5198), 675–9.
[10] Strobel, Scott A.; Cech, Thomas R.. Exocyclic Amine of the Conserved G.cntdot.U Pair at the Cleavage Site of the Tetrahymean Ribozyme Contributes to 5'-Splice Site Selection and Transition State Stabilization. Biochemistry (1996), 35(4), 1201–11.
[11] Sullenger, Bruce A.; Cech, Thomas R.. Ribozyme-mediated repair of defective mRNA by targeted trans-splicing. Nature (London) (1994), 371(6498), 619–22.
[12] Robertson, H. D.; Altman, S.; Smith, J. D.. J. Biol. Chem., 247, 5243–5251 (1972).
[13] Forster, Anthony C.; Altman, Sidney. External guide sequences for an RNA enzyme. Science (Washington, D. C., 1883-) (1990), 249(4970), 783–6.
[14] Yuan, Y.; Hwang, E. S.; Altman, S.. Targeted cleavage of mRNA by human RNase P. Proc. Natl. Acid. Sci. USA (1992) 89, 8006–10.
[15] Harris, Michael E.; Pace, Norman R.. Identification of phosphates involved in catalysis by the ribozyme RNAase P RNA. RNA (1995), 1(2), 210–18.
[16] Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
[17] Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
[18] Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationshps. Biochemistry (1995), 34(9), 2965–77.
[19] Zimmerly, Steven; Guo, Huatao; Eskes, Robert; Yang, Jian; Periman, Philip S.; Lambowitz, Alan M.. A group II intron RNA is a catalyst component of a DNA endonuclease involved in intron mobility. Cell (Cambridge, Mass.) (1995), 83(4), 529–38.
[20] Griffin, Edmund A., Jr.; Qin, Zhifeng; Michels, Williams J., Jr.; Pyle, Anna Marie. Group II introns ribozymes that cleave DNA and RNA linkages with similar efficiency, and lack contacts with substrate 2'-hydroxyl groups. Chem. Biol. (1995), 2(11), 761–70.
[21] Michel, Francois; Ferat, Jean Luc. Structure and activities of group II introns. Annu. Rev. Biochem. (1995), 64, 435–61.
[22] Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
[23] Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.
[24] Guo, Hans C. T.; Collins, Richard A.. Efficient trans-cleavage of a stem-loop RNA substrate by a ribozyme derived from Neurospora VS RNA. EMBO J. (1995), 14(2), 368–76.
[25] Scott, W. G., Finch, J. T., Aaron, K.. The crystal structure of an all RNA hammerhead ribozyme: A proposed mechanism for RNA catalytic cleavage. Cell, (1995), 81, 991–1002.
[26] McKay, Structure and function of the hammerhead ribozyme: an unfinished story. RNA, (1996), 2, 395–403.
[27] Long, D., Uhlenbeck, O., Hertel, K.. Ligation with hammerhead ribozymes. U.S. Pat. No. 5,633,133.
[28] Hertel, K. J., Herschlag, D., Uhlenbeck, O.. A kinetic and thermodynamic framework for the hammerhead ribozyme reaction. Biochemistry, (1994) 33, 3374–3385. Beigelman, L., et al., Chemical modifications of hammerhead ribozymes. J. Biol. Chem., (1995) 270, 25702–25708.
[29] Beigelman, L., et al., Chemical modifications of hammerhead ribozymes. J. Biol. Chem., (1995) 270, 25702–25708.

TABLE 1-continued

Characteristics of naturally occurring ribozymes

[30]Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
[31]Chowrira, Bharat M.; Berzal-Herranz, Alfredo; Burke, John M.. Novel guanosine requirement for catalysis by the hairpin ribozyme. Nature (London) (1991), 354(6351), 320–2.
[32]Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
[33]Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
[34]Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
[35]Hegg, Lisa A.; Fedor, Martha J.. Kinetics and Thermodynamics of Intermolecular Catalysis by Hairpin Ribozymes. Biochemistry (1995), 34(48), 15813–28.
[36]Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
[37]Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
[38]Perrotta, Anne T.; Been, Michael D.. Cleavage of oligoribonucleotides by a ribozyme derived from the hepatitis .delta. virus RNA sequence. Biochemistry (1992), 31(1), 16–21.
[39]Perrotta, Anne T., Been, Michael D.. A pseudoknot-like structure required for efficient self-cleavage of hepatitis delta virus RNA. Nature (London) (1991), 350(6317), 434–6.
[40]Puttaraju, M.; Perrotta, Anne T.; Been, Michael D.. A circular trans-acting hepatitis delta virus ribozyme. Nucleic Acids Res. (1993), 21(18), 4253–8.

TABLE II 2.5 μmol RNA Synthesis Cycle

| Reagent | Equivalents | Amount | Wait Time* |
|---|---|---|---|
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

I claim:

1. A method for identifying a gene that modulates a process in a biological system comprising the steps of:
   a) introducing a library of nucleic acid catalysts into a biological system under conditions suitable for modulating a process in the biological system, wherein each nucleic acid catalyst comprises a substrate binding domain and a catalytic domain and the substrate binding domain comprises a random sequence;
   b) determining the nucleotide sequence of at least a portion of the substrate binding domain of any nucleic acid catalyst in the biological system in which the process has been modulated; and
   c) identifying a gene that modulates a process in a biological system using the nucleotide sequence from step (b).

2. A method for identifying a gene involved in a biological process comprising the steps of:
   a) introducing a library of nucleic acid catalysts into a biological system under conditions suitable for altering a process in the biological system, wherein each nucleic acid catalyst comprises a substrate binding domain and a catalytic domain and the substrate binding domain comprises a random sequence;
   b) identifying any nucleic acid catalyst in the biological system in which the biological process has been altered; and
   c) determining the nucleotide sequence of at least a portion of the substrate binding domain of any nucleic acid catalyst from step (b) to identify a gene involved in said biological process.

3. A method comprising the steps of:
   a) providing a random binding arm nucleic acid catalyst library to a biological system under conditions suitable for a nucleic acid catalyst from the library to down-regulate the expression of a gene;
   b) determining the biological system in which the expression of a gene has been down-regulated;
   c) determining the nucleotide sequence of at least one portion of the binding arm of the nucleic acid catalyst in the biological system of step (b); and
   d) identifying the gene which expression is down-regulated using the nucleotide sequence from step (c).

4. The method of any of claims 1–3, wherein said nucleic acid catalyst is in a group I intron ribozyme motif, group II intron ribozyme motif hepatitis delta virus ribozyme motif, VS ribozyme motif or RNase P ribozyme motif.

5. The method of any of claims 1–3, wherein said nucleic acid catalyst is in a hammerhead ribozyme motif.

6. The method of any of claims 1–3, wherein said nucleic acid catalyst is in a hairpin ribozyme motif.

7. The method of any of claims 1–3, wherein said nucleic acid catalyst is in a catalytic DNA motif.

8. The method of any of claims 1–3, wherein said biological system is a bacterial cell.

9. The method of any of claims 1–3, wherein said biological system is of plant origin.

10. The method of any of claims 1–3, wherein said biological system is of mammalian origin.

11. The method of any of claims 1–3, wherein said biological system is of yeast origin.

12. The method of any of claims 1–3, wherein said biological system is Drosophila.

13. The method of claim 1 or claim 2, wherein said process is selected from the group consisting of growth, proliferation, apoptosis, morphology, angiogenesis, differentiation, migration, viral multiplication, drug resistance, signal transduction, cell cycle regulation, temperature sensitivity and chemical sensitivity.

14. The method of any of claims 1–3, wherein said library of nucleic acid catalysts is encoded by an expression vector in a manner which allows expression of said nucleic acid catalysts.

15. The method of claim 14, wherein said expression vector comprises:
a) a transcription initiation region;
b) a transcription termination region; and
c) a sequence encoding at least one said nucleic acid catalyst, wherein said sequence is operably linked to said initiation region and said termination region, in a manner which allows expression or delivery or expression and delivery of said nucleic acid catalyst.

16. The method of claim 14, wherein said expression vector comprises:
a) a transcription initiation region;
b) a transcription termination region;
c) an open reading frame for a polypeptide; and
d) a sequence encoding at least one said nucleic acid catalyst, wherein said sequence is operably linked to the 3'-end of said open reading frame; wherein said sequence is operably linked to said initiation region, said open reading frame and said termination region, in a manner which allows expression or delivery or expression and delivery of said nucleic acid catalyst.

17. The method of claim 14, wherein said expression vector comprises:
a) a transcription initiation region;
b) a transcription termination region;
c) an intron; and
d) a sequence encoding at least one said nucleic acid catalyst, wherein said sequence is operably linked to said initiation region, said intron and said termination region, in a manner which allows expression or delivery or expression and delivery of said nucleic acid catalyst.

18. The method of claim 14, wherein said expression vector comprises:
a) a transcription initiation region;
b) a transcription termination region;
c) an intron;
d) an open reading frame for a polypeptide; and
e) a sequence encoding at least one said nucleic acid catalyst, wherein said sequence is operably linked to the 3'-end of said open reading frame; wherein said sequence is operably linked to said initiation region, said intron, said open reading frame and said termination region, in a manner which allows expression or delivery or expression and delivery of said nucleic acid catalyst.

19. The method of claim 14, wherein said expression vector is derived from a retrovirus.

20. The method of claim 14, wherein said expression vector is derived from an adenovirus.

21. The method of claim 14, wherein said expression vector is derived from an adenoassociated virus.

22. The method of claim 14, wherein said expression vector is derived from an alphavirus.

23. The method of claim 14, wherein said expression vector is derived from a bacterial plasmid.

24. The method of claim 14, wherein said expression vector is operably linked to a RNA polymerase II promoter element.

25. The method of claim 14, wherein said expression vector is operably linked to a RNA polymerase III promoter element.

26. The method of claim 25, wherein said RNA polymerase III promoter is derived from a transfer RNA gene.

27. The method of claim 25, wherein said RNA polymerase III promoter is derived from a U6 small nuclear RNA gene.

28. The method of claim 25, wherein the nucleic acid catalyst comprises a sequence at its 5'-end homologous to the terminal 27 nucleotides encoded by said U6 small nuclear RNA gene.

29. The method of claim 26, wherein said RNA polymerase III promoter is derived from a TRZ RNA gene.

30. The method of any of claims 1–3, wherein said biological system is of an eukaryotic origin.

31. The method of any of claims 1–3, wherein said biological system is of an prokaryotic origin.

32. The method of any of claims 1–3, wherein said biological system is of an archaebacterial origin.

33. The method of any of claims 1–3, wherein said substrate binding domain is of a length between 12 and 100 nucleotides.

34. The method any of claims 1–3, wherein said substrate binding domain is of a length between 14 and 24 nucleotides.

35. The method of any of claims 1–2, wherein said substrate binding domain comprises one substrate binding arm.

36. The method of any of claims 1–2, wherein said substrate binding domain comprises two substrate binding arms.

37. The method of claim 36, wherein said substrate binding arms are of similar length.

38. The method of claim 36, wherein said substrate binding arms are of different length.

39. The method of any of claims 1–3, wherein said library of nucleic acid catalysts is a multimer library.

* * * * *